(12) United States Patent
Bowser et al.

(10) Patent No.: US 12,178,990 B2
(45) Date of Patent: *Dec. 31, 2024

(54) COMPONENT POSITIONING OF A LINEAR SHUTTLE PUMP

(71) Applicant: Insulet Corporation, Acton, MA (US)

(72) Inventors: Andrew Bowser, Barrington, RI (US); Steven Cardinali, Tewksbury, MA (US)

(73) Assignee: INSULET CORPORATION, Acton, MA (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/721,613

(22) Filed: Apr. 15, 2022

(65) Prior Publication Data

US 2022/0233764 A1 Jul. 28, 2022

Related U.S. Application Data

(63) Continuation of application No. 16/674,722, filed on Nov. 5, 2019, now Pat. No. 11,369,735.

(51) Int. Cl.
*A61M 5/142* (2006.01)
*A61M 5/145* (2006.01)
*A61M 5/168* (2006.01)

(52) U.S. Cl.
CPC ...... *A61M 5/14244* (2013.01); *A61M 5/1452* (2013.01); *A61M 5/168* (2013.01); *A61M 2205/3306* (2013.01)

(58) Field of Classification Search
CPC ...... A61M 2205/3306; A61M 5/14244; A61M 5/1452; A61M 5/14526;

(Continued)

(56) References Cited

U.S. PATENT DOCUMENTS 4,234,223 A * 11/1980 O'Neil .................... B25B 7/126
 294/203
4,277,226 A 7/1981 Archibald
(Continued)

FOREIGN PATENT DOCUMENTS

CN 101721761 A 6/2010
CN 102498292 B 7/2015
(Continued)

OTHER PUBLICATIONS

International Search Report and Written Opinion for International Patent Application No. PCT/US2022/029012, mailed Aug. 19, 2022, 12 pages.

(Continued)

*Primary Examiner* — Quynh-Nhu H. Vu
(74) *Attorney, Agent, or Firm* — GOODWIN PROCTER LLP

(57) ABSTRACT

Disclosed herein are wearable drug delivery devices and methods for component positioning of a linear shuttle pump. In some approaches, a pump may include a pump chamber operably coupled with a piston, and a detent apparatus, wherein the detent apparatus comprises a detent body, a detent arm, and a detent engagement member. The detent engagement member may be retained in direct physical contact with first or second arrest locations of either the detent body or the detent arm. The pump may further include a piston grip coupled to the piston, the piston grip including a grip component engaged with an exterior of the piston. Movement of the piston grip may cause the piston to move axially relative to the pump chamber to control receipt and delivery of a liquid drug.

19 Claims, 17 Drawing Sheets

(58) Field of Classification Search
CPC .... A61M 2005/14533; A61M 5/14546; A61M 2005/14553; A61M 5/168; A61M 5/172
See application file for complete search history.

(56) References Cited

U.S. PATENT DOCUMENTS

| | | | | |
|---|---|---|---|---|
| 4,424,720 | A * | 1/1984 | Bucchianeri | B23Q 5/406 |
| | | | | 74/424.78 |
| 4,991,743 | A | 2/1991 | Walker | |
| 5,921,967 | A * | 7/1999 | Sadowski | A61M 5/30 |
| | | | | 604/218 |
| 6,740,059 | B2 | 5/2004 | Flaherty | |
| 7,137,964 | B2 | 11/2006 | Flaherty | |
| 7,641,649 | B2 * | 1/2010 | Moberg | A61M 5/158 |
| | | | | 604/890.1 |
| 8,920,376 | B2 * | 12/2014 | Caffey | A61M 5/14526 |
| | | | | 604/173 |
| 2003/0055380 | A1 | 3/2003 | Flaherty | |
| 2003/0198558 | A1 * | 10/2003 | Nason | F04B 17/00 |
| | | | | 417/328 |
| 2005/0015056 | A1 * | 1/2005 | Duchon | A61M 5/14546 |
| | | | | 604/218 |
| 2006/0106347 | A1 * | 5/2006 | Fago | A61M 5/14546 |
| | | | | 604/523 |
| 2011/0073620 | A1 | 3/2011 | Verrilli | |
| 2012/0172817 | A1 | 7/2012 | Bruggemann et al. | |
| 2013/0060196 | A1 * | 3/2013 | O'Connor | A61M 5/172 |
| | | | | 604/152 |
| 2015/0051487 | A1 | 2/2015 | Uber et al. | |
| 2016/0213851 | A1 | 7/2016 | Weibel et al. | |
| 2017/0290975 | A1 | 10/2017 | Barmaimon et al. | |

FOREIGN PATENT DOCUMENTS

| | | |
|---|---|---|
| CN | 204972511 U | 1/2016 |
| CN | 105764543 B | 7/2016 |
| CN | 206175149 U | 5/2017 |
| CN | 107096091 A | 8/2017 |
| CN | 107847673 A | 3/2018 |
| CN | 108472441 A | 8/2018 |
| EP | 1874390 B1 | 10/2014 |
| JP | 2009514580 A | 4/2009 |
| JP | 2017513577 A | 6/2017 |
| KR | 20050092105 A | 9/2005 |
| WO | 2013149186 A1 | 10/2013 |
| WO | 2021016452 A1 | 1/2021 |

OTHER PUBLICATIONS

International Search Report and Written Opinion, Application No. PCT/US2022/016713, mailed Aug. 5, 2022, 19 pages.

* cited by examiner

COMPONENT POSITIONING OF A LINEAR SHUTTLE PUMP

RELATED APPLICATIONS

This application is a continuation of U.S. patent application Ser. No. 16/674,722, filed Nov. 5, 2019, the contents of which are incorporated herein by reference in their entirety.

FIELD

Embodiments herein generally relate to medication delivery. More particularly, embodiments herein relate to wearable drug delivery devices and methods for component positioning of a linear shuttle pump.

BACKGROUND

Many wearable drug delivery devices include a reservoir for storing a liquid drug. A drive mechanism, such as a pump including a pump chamber and piston, is operated to expel the stored liquid drug from the reservoir for delivery to a user. A problem with known devices is that the delivery rate accuracy suffers when the volume of drug is small. Such inaccuracies arise in many cases from the drive mechanism(s) employed, which gives rise to variations in delivery rates. Accordingly, there is a need to provide a wearable drug delivery device capable of regulating drug delivery dosages while simultaneously verifying drive mechanism positioning and sequencing.

SUMMARY

In one approach of the disclosure, a pump may include a pump chamber operably coupled with a piston, and a detent apparatus coupled to the pump chamber or the piston. The detent apparatus may include a detent body, a detent arm, and a detent engagement member, wherein in a first position the detent engagement member is retained in contact with a first arrest location of either the detent body or the detent arm, and wherein in a second position the detent engagement member is retained in contact with a second arrest location of either the detent body or the detent arm. The pump may further include a piston grip coupled to the piston, the piston grip including a grip component engaged with an exterior of the piston, wherein movement of the piston grip causes the piston to move axially relative to the pump chamber to control receipt and delivery of a liquid drug.

In another approach of the disclosure, a linear volume shuttle pump may include a pump chamber operably coupled with a piston, and a detent apparatus coupled to the pump chamber or the piston. The detent apparatus may include a detent body, a detent arm, and a detent engagement member, wherein the detent engagement member is operable to move between first and second arrest locations disposed along the detent body or the detent arm. The linear volume shuttle pump may further include a piston grip coupled to the piston, the piston grip including a grip component engaged with an exterior of the piston, wherein movement of the piston grip causes the piston to move axially relative to the pump chamber to control receipt of a liquid drug from a reservoir and delivery of the liquid drug from the pump chamber.

In yet another approach of the disclosure, a linear volume shuttle pump may include a pump chamber operably coupled with a piston, and a detent apparatus coupled to the pump chamber or the piston. The detent apparatus may include a detent body, a detent arm, and a detent engagement member, wherein the detent engagement member is operable to move between first and second arrest locations disposed along the detent body or the detent arm. The linear volume shuttle pump may further include a piston grip coupled to the piston, the piston grip including a grip component engaged with an exterior of the piston, wherein movement of the piston grip causes the piston to move axially relative to the pump chamber to control receipt of a liquid drug from a reservoir and delivery of the liquid drug from the pump chamber. The linear volume shuttle pump may further include a contact extending from the detent apparatus or the piston grip, the contact operable to make or break contact with one or more contact members coupled to a pump housing.

BRIEF DESCRIPTION OF DRAWINGS

The accompanying drawings illustrate example approaches of the disclosure, including the practical application of the principles thereof, as follows.

Figure 1:
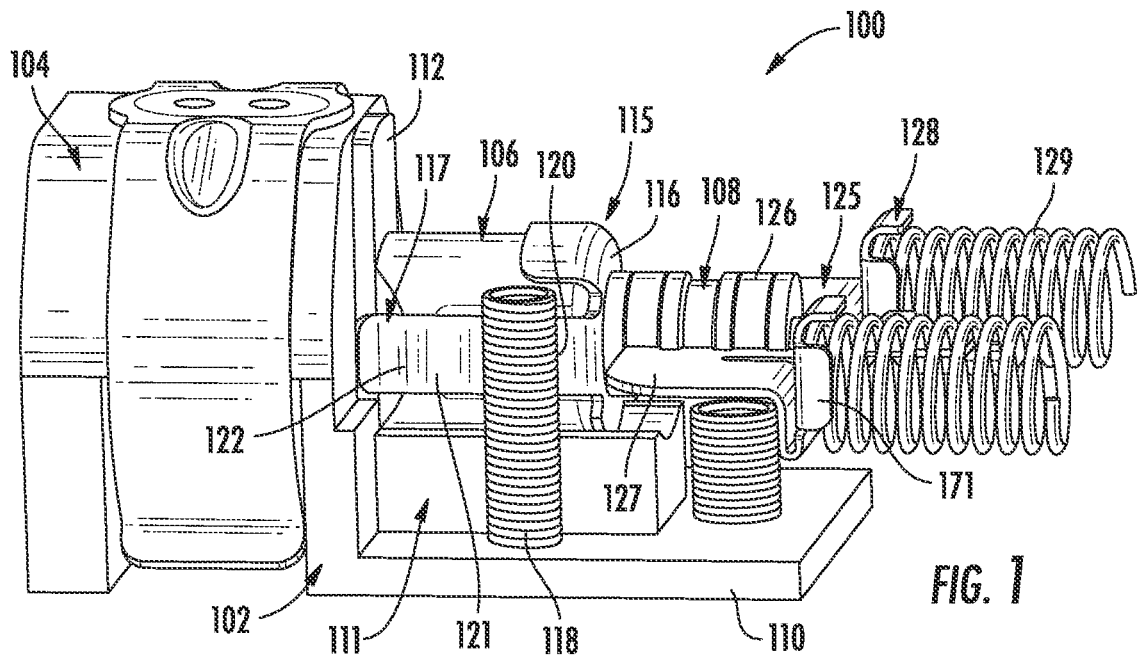
FIG. 1 illustrates a perspective view of an example linear volume shuttle fluid pump according to embodiments of the present disclosure.

The drawings are not necessarily to scale. The drawings are merely representations, not intended to portray specific parameters of the disclosure. The drawings are intended to depict example embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, some reference numbers may be omitted in certain drawings.

DETAILED DESCRIPTION

Various approaches in accordance with the present disclosure will now be described more fully hereinafter with reference to the accompanying drawings, where embodiments of the methods are shown. The approaches may be embodied in many different forms and are not to be construed as being limited to the embodiments set forth herein. Instead, these embodiments are provided so this disclosure will be thorough and complete, and will fully convey the scope of the approaches to those skilled in the art.

Various examples disclosed herein provide a drive mechanism and/or pump system with the ability to control and verify pump sequencing. As a result, a drug delivery device that contains a reservoir and a pump may be made more reliable and thus safer for users.

Various examples described herein enable a pump, such as a linear volume shuttle pump (LVSP), to execute a pumping cycle in a proper sequence. At any given time during pump actuation, it is beneficial to know the location of different pump components, namely a pump chamber and a piston, as the pump chamber and the piston are responsible for drawing in and expelling fluid. Knowing the location of both the pump chamber and the piston also indicates whether the pump operates in a designed sequence. In some examples of the present disclosure, one or more mechanical detents and sensing/sequencing mechanisms may be implemented with the pump to both control the position of the pump chamber and the piston, thus maintaining the pump cycling in the proper sequence, and to provide feedback as to the position of the pump chamber and/or the piston. As will be described in greater detail herein, multiple methods and devices may be implemented for tracking the location of the chamber and the piston, such as electromechanical contacts, optical sensing, and/or capacitance sensing.

Figure 2:
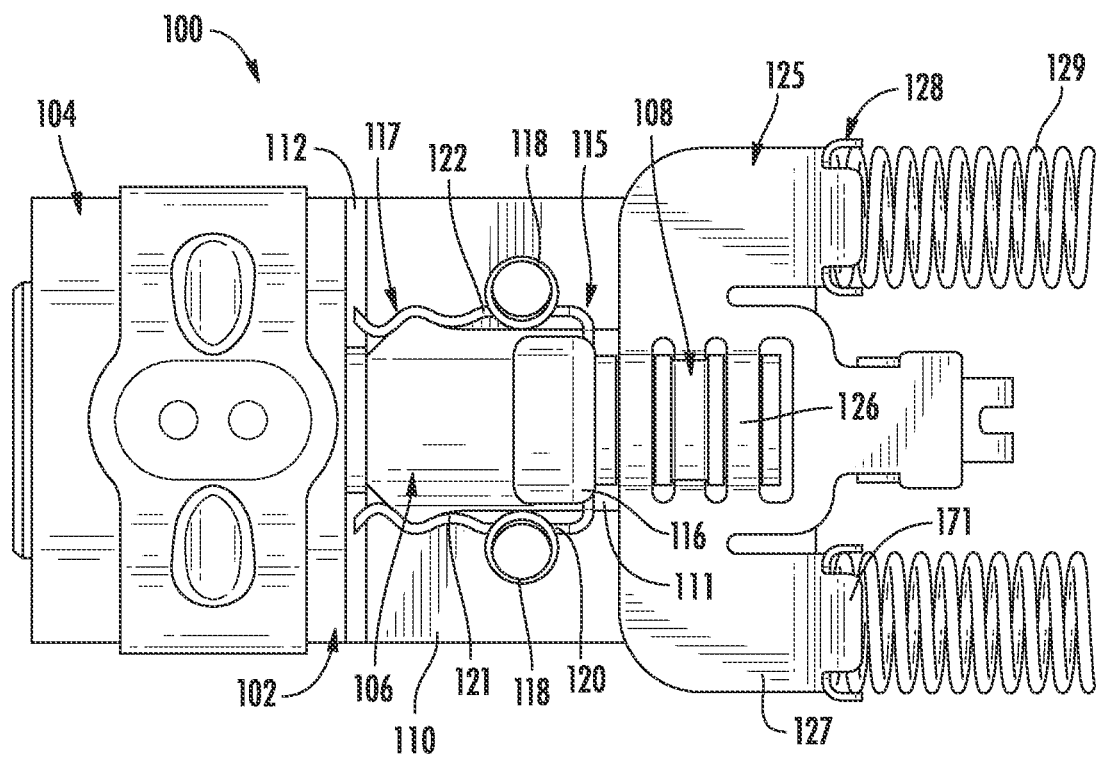
FIG. 2 illustrates a top view of the linear volume shuttle fluid pump depicted in FIG. 1 according to embodiments of the present disclosure.

FIGS. 1-2 illustrate a linear volume shuttle fluid pump 100 (hereinafter "pump") according to embodiments of the present disclosure. As shown, the pump 100 may include a pump housing 102 coupling together a fluid reservoir 104, a pump chamber 106, and a piston 108. In some embodiments, the fluid reservoir 104 may contain a fluid or liquid drug. The pump housing 102 may include a base 110, a chassis 111 extending from the base 110 for retaining the pump chamber 106, and a reservoir wall 112 operable to interface with the pump chamber 106, as will be described in greater detail herein. Although non-limiting, the pump housing 102 may be formed from an injection molded plastic or other similar material.

Although not shown, the pump chamber 106 may include an inlet pathway or component and an outlet pathway or component. A liquid or fluid can enter the pump chamber 106 through the inlet pathway and can exit the pump chamber 106 through the outlet pathway. One or more plunger components may operate with the inlet and outlet pathways to draw a fluid into the pump chamber 106 and to expel the fluid from the pump chamber 106. In various examples, the pump chamber 106 may be coupled to the fluid reservoir 104 that stores a fluid or liquid drug. For example, the inlet may be coupled to the fluid reservoir 104 and the outlet pathway may be coupled to a fluid path component (not shown) that is coupled to a patient or user that is to receive the liquid drug stored in the fluid reservoir 104.

As further shown, the pump 100 may include a detent apparatus 115 coupled to the pump chamber 106. In some embodiments, the detent apparatus 115 may include a detent cap or body 116, one or more detent arms 117 extending from the detent body 116, and one or more detent engagement members 118. The detent body 116 may extend over and/or abut one end of the pump chamber 106. In some embodiments, the detent body 116 may further abut the piston 108, wherein an opening (not shown) of the detent body 116 may allow a rod of the piston 108 to pass therethrough.

The detent arms 117 may include a first arrest location 120 and a second arrest location 121. As shown, the first and second arrest locations 120, 121 may correspond to recesses or valleys disposed between one or more peaks 122. The first and second arrest locations 120, 121 may be curved to generally compliment the dimensions of the detent engagement member 118, which in this case, is a helical spring extending from the base 110 of the pump housing 102. The first and second arrest locations 120, 121 allow discrete positioning of the pump chamber 106 and/or the piston 108 by adding additional frictional forces to restrict movement of the detent body 116 prior to a desired time.

In the non-limiting embodiment depicted, the detent engagement member 118 is in contact with the first arrest location 120 of the detent arm 117 when in a first position. In a second position, the detent engagement member 118 may be in contact with the second arrest location 121 of the detent arm 117. The detent engagement member 118 may change between the first position and second position as the pump chamber 106 moves relative to the fluid reservoir 104.

As further shown, the pump 100 may include a piston grip 125 coupled to the piston 108. The piston grip 125 may include one or more grip components 126 engaged with an exterior of the piston 108. During operation, movement of the piston grip 125 causes the piston 108 to move axially relative to the pump chamber 106 to control receipt and delivery of a liquid drug within the pump chamber 106. The piston grip 125 may be actuated by a variety of mechanisms and/or actuators. In various examples, the piston grip 125 may be actuated by an actuator capable of producing reciprocating motion, for example, a piezoelectric-based actuator, a solenoid-based actuator, a Nitinol-based actuator, a spring-based actuator, a rotary motor with a gear drain, a direct current (DC) motor, or any combination thereof. As a result, a desired effect of shuttling fluid (e.g., a liquid drug) may be achieved.

In some embodiments, the piston grip 125 includes a grip body 127 extending on opposite sides of the piston 108. The grip body 127 may be a generally planar component including one or more spring footers 128 extending therefrom. As shown, each spring footer 128 may include one or more tabs 171 to engage and retain therein a side spring 129. In this embodiment, the side springs 129 may be disposed on opposite sides of the piston 108, parallel to a central axis (not shown) extending through the piston 108, the pump chamber 106, and the detent body 116. The side springs 129 may provide a spring force to bias the piston grip 125, and thus the piston 108, towards the pump chamber 106.

Figure 3:
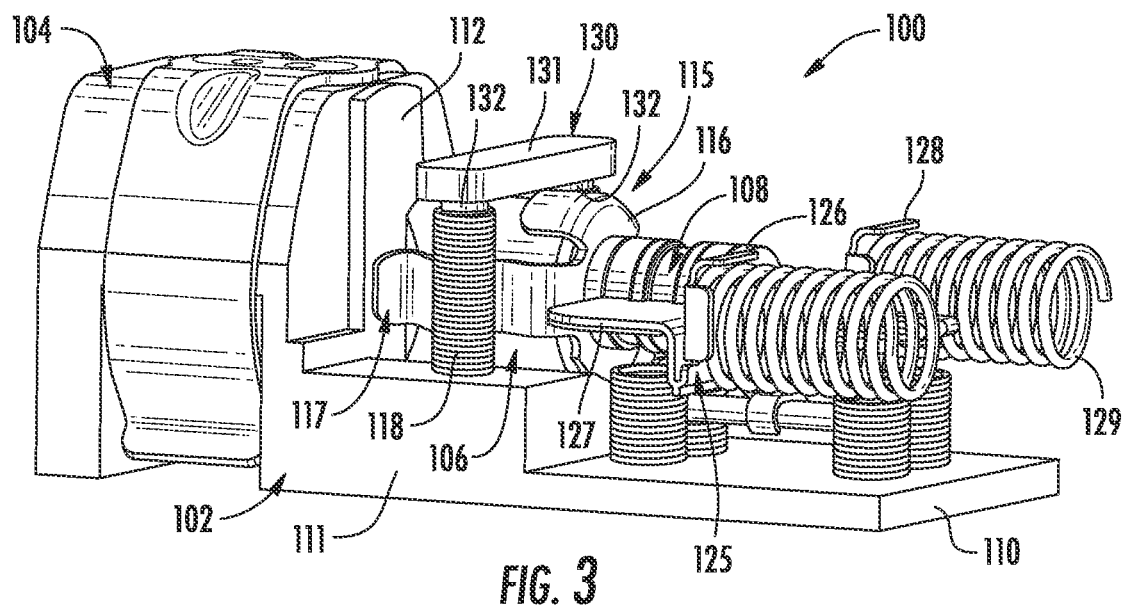
FIG. 3 illustrates a perspective view of an example linear volume shuttle fluid pump according to embodiments of the present disclosure.
Figure 4:
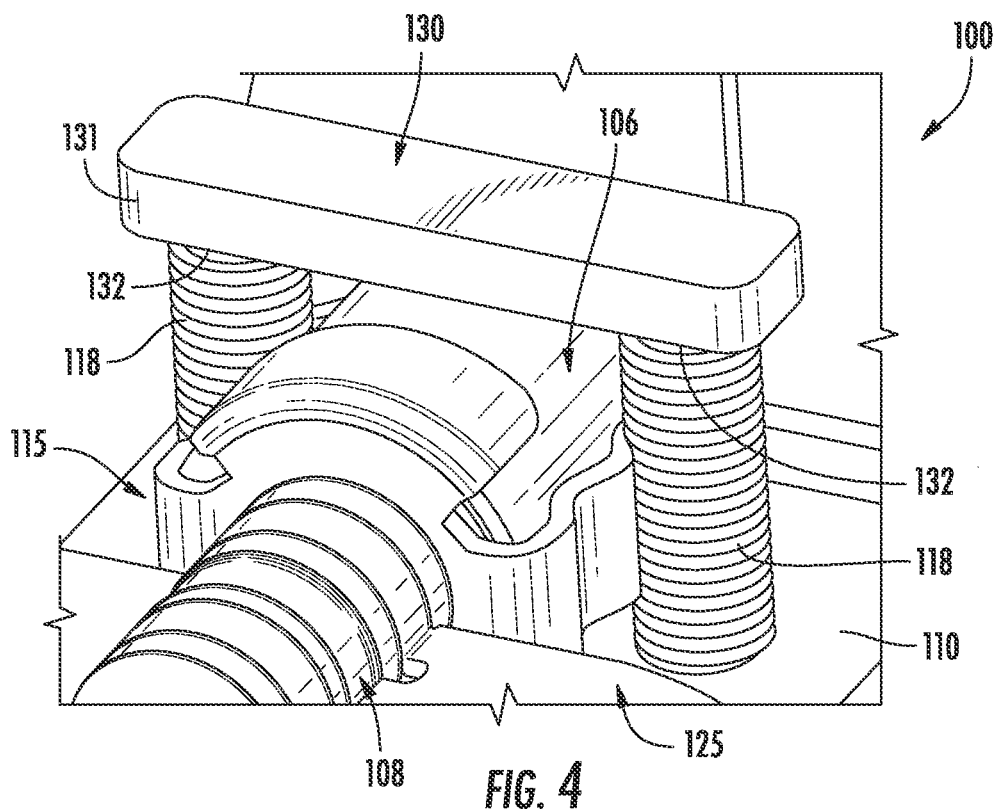
FIG. 4 illustrates another view of the linear volume shuttle fluid pump depicted in FIG. 3 according to embodiments of the present disclosure.

As shown in FIGS. 3-4, in some embodiments, the pump 100 may include a detent cap 130 positioned atop the detent engagement members 118 to provide support/rigidity thereto, as the detent engagement members 118 may be prone to unpredictable bistable behavior. In some embodiments, the detent cap 130 may include an elongate body 131 extending between free ends of each of the detent engagement members 118. As shown, a vertical shaft 132, which may extend from an underside of the elongate body 131, extends into a center cavity defined by the helical structure of each of the detent engagement members 118.

Figure 5:
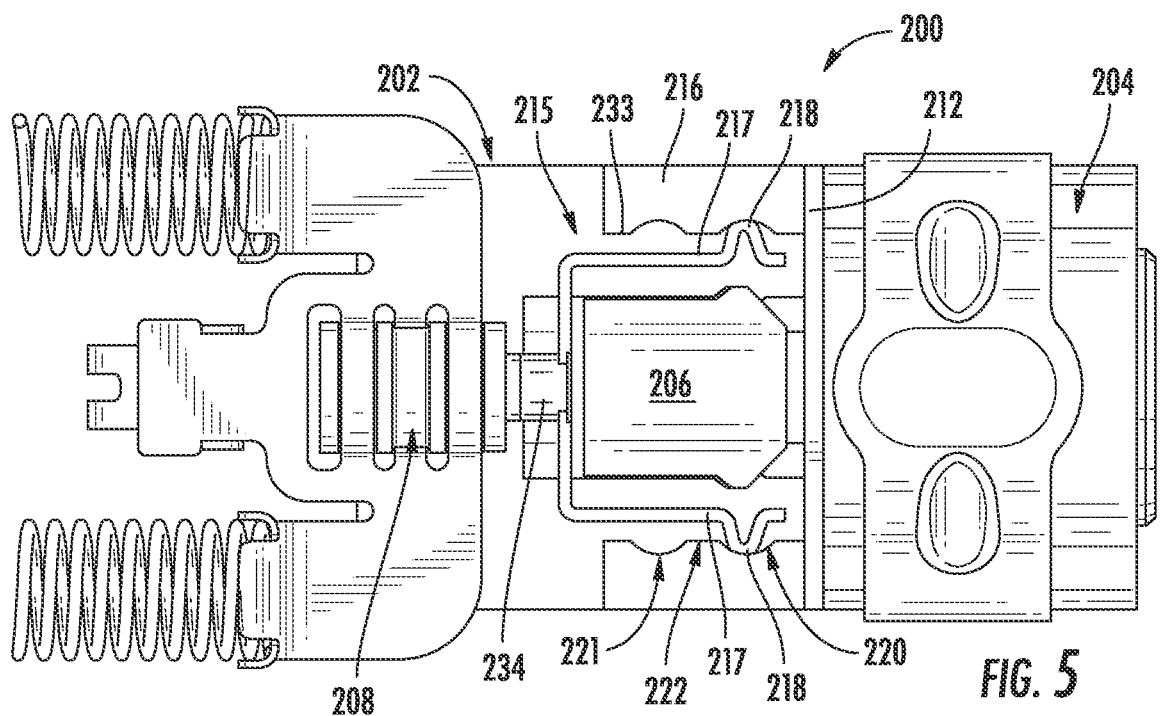
FIG. 5 illustrates a top view of an example linear volume shuttle fluid pump according to embodiments of the present disclosure.
Figure 6:
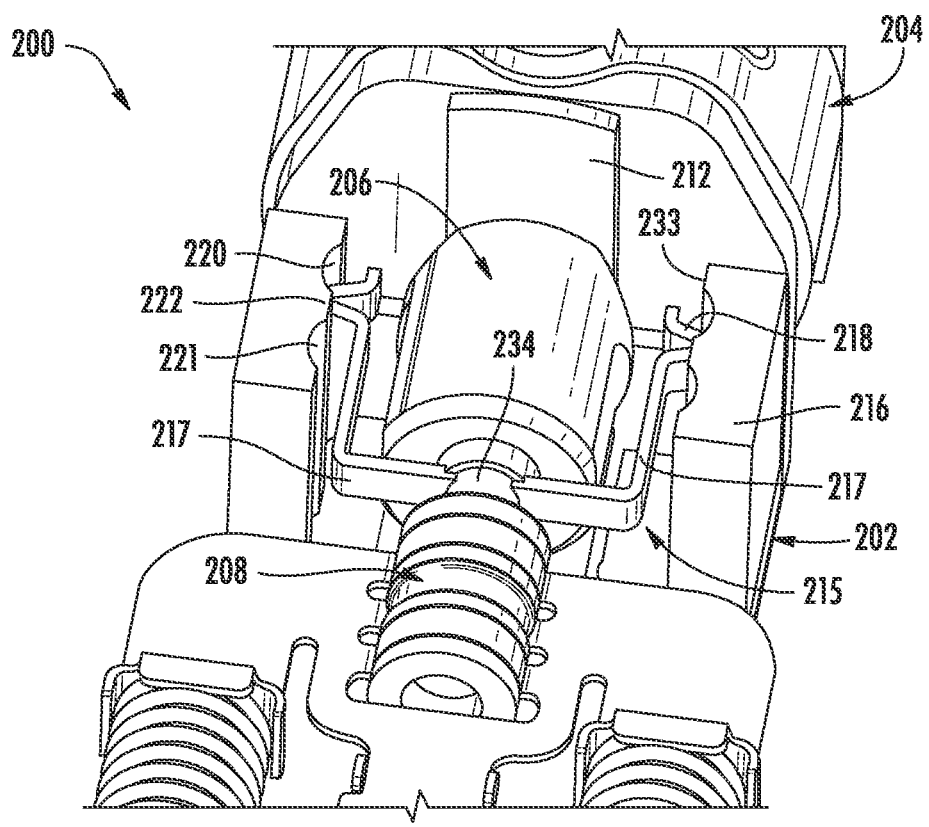
FIG. 6 illustrates a perspective view of the linear volume shuttle fluid pump depicted in FIG. 5 according to embodiments of the present disclosure.

Turning now to FIGS. 5-6, a pump 200 according to embodiments of the present disclosure will be described in greater detail. The pump 200 may be similar in many aspects to the pump 100 described above. As such, only certain aspects of the pump 200 may be described hereinafter for the sake of brevity. In this embodiment, the pump 200 may include a detent apparatus 215 coupled to a piston rod 234 of a piston 208. The detent apparatus 215 may include a detent body 216, which may be coupled to or integrally formed with a housing 202. The detent apparatus 215 may further include one or more detent arms 217 extending from the piston rod 234, wherein each detent arm 217 includes one or more detent engagement members 218 engaged with the detent body 216. In some embodiments, the detent arms 217 may be rigid or semi-rigid elements extending towards a reservoir wall 212 of a fluid reservoir 204. Each of the detent arms 217 may be permit a degree of radial flexing relative to a pump chamber 206 as the pump chamber 206 moves axially with respect to the fluid reservoir 204.

The detent body 216 may include a first arrest location 220 and a second arrest location 221. As shown, the first and second arrest locations 220, 221 may correspond to recesses or valleys disposed between protrusions or peaks 222 along a sidewall 233 of the detent body 216. In some embodiments, the first and second arrest locations 220, 221 may be curved or notched to generally compliment the dimensions of the detent engagement members 218. The first and second arrest locations 220, 221 allow discrete positioning of the pump chamber 206 and/or the piston 208 during use. For example, as the piston 208 moves relative to the fluid reservoir 204, each detent engagement member 218 may move from the first arrest location 220 to the second arrest location 221.

Figure 7:
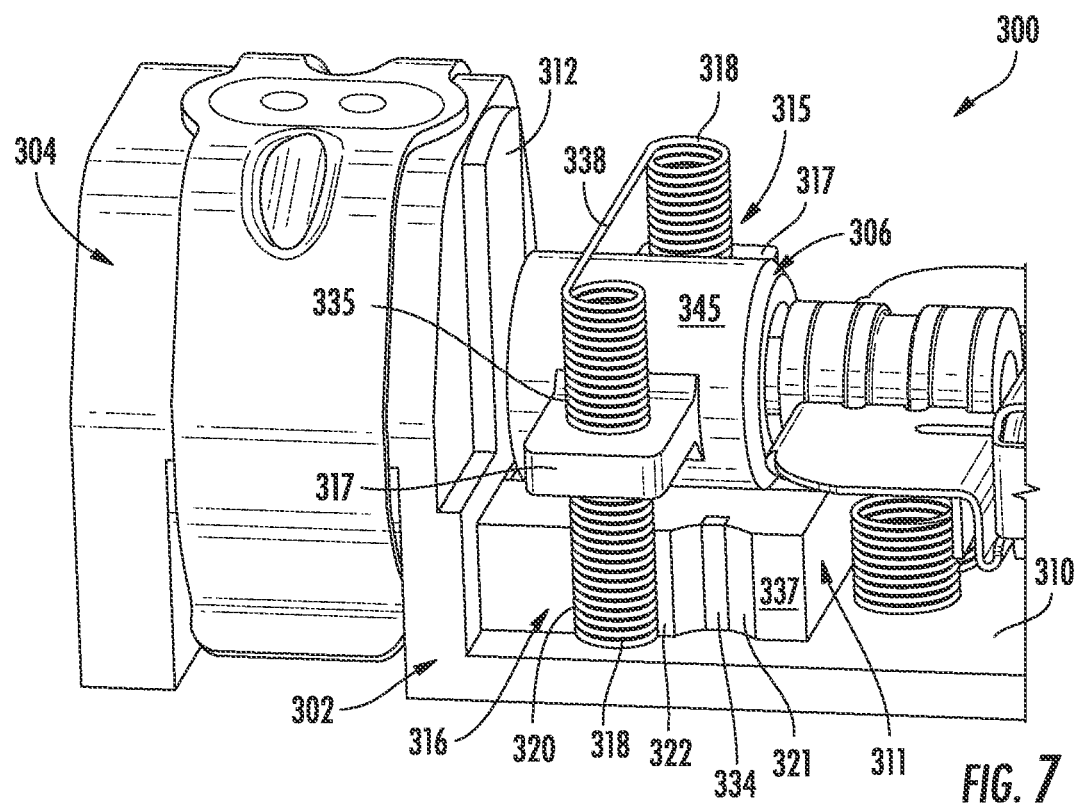
FIG. 7 illustrates a perspective view of an example linear volume shuttle fluid pump according to embodiments of the present disclosure.
Figure 8:
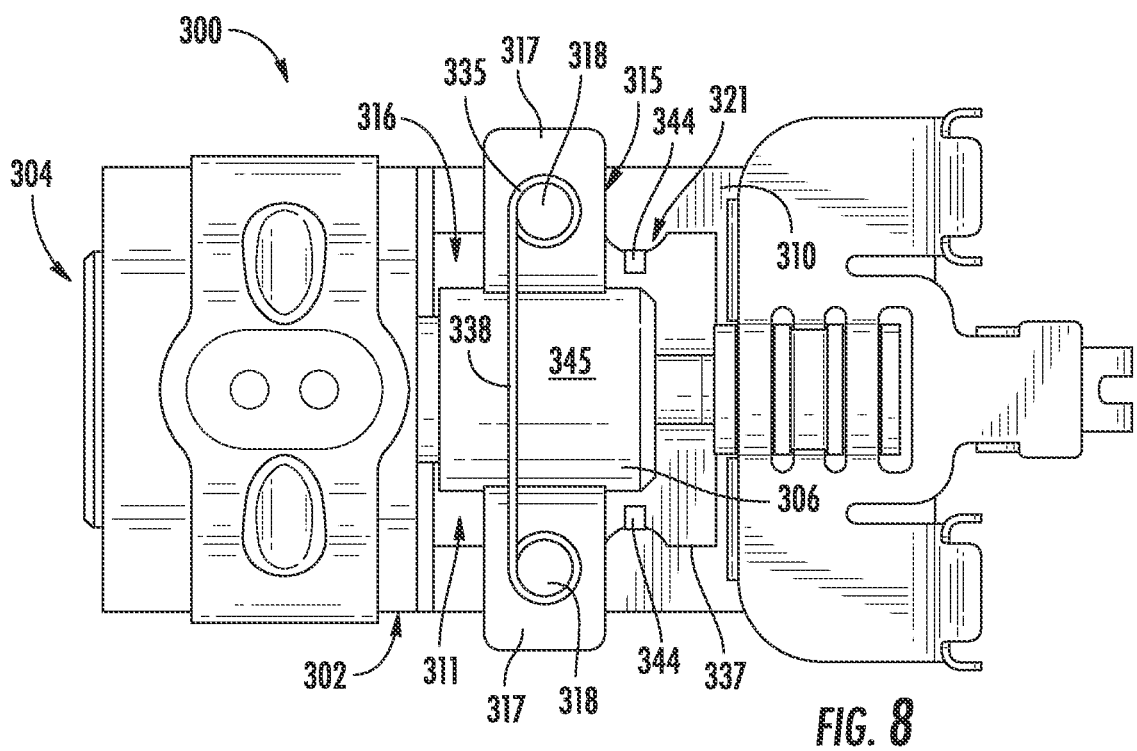
FIG. 8 illustrates a top view of the linear volume shuttle fluid pump depicted in FIG. 7 according to embodiments of the present disclosure.

Turning now to FIGS. 7-8, a pump 300 according to embodiments of the present disclosure will be described in greater detail. The pump 300 may be similar in many aspects to the pumps 100 and 200 described above. As such, only certain aspects of the pump 300 may be described hereinafter for the sake of brevity. In this embodiment, the pump 300 may include a detent apparatus 315 coupled to a pump chamber 306. The detent apparatus 315 may include a detent body 316, which may be coupled to or integrally formed with a pump housing 302. For example, the detent body 316 may correspond to an outer surface 337 of a chassis 311 extending from a base 310 of the pump housing 302.

The detent apparatus 315 may further include one or more detent arms 317 extending from an exterior surface 345 of the pump chamber 306. As shown, the detent arms 317 may generally extend radially away from the pump chamber 306. Each detent arm 317 may include an opening 335 receiving a detent engagement member 318 therein. In this embodiment, the detent engagement members 318 may be helical springs extending from the base 310 of the pump housing 302. As shown, the detent engagement members 318 may be joined together by a connector 338 to provide rigidity and support thereto. Furthermore, the connector 338 may provide an electrical connection between each of the detent engagement members 318.

The detent body 316 may include a first arrest location 320 and a second arrest location 321. As shown, the first and second arrest locations 320, 321 may correspond to recesses or valleys disposed between protrusions or peaks 322 along the outer surface 337 of the detent body 316. In some embodiments, the first and second arrest locations 320, 321 may be curved or notched to generally compliment the dimensions of the detent engagement members 318. The first and second arrest locations 320, 321 allow discrete positioning of the pump chamber 306 and/or the piston 308 during use.

In this embodiment, the detent body 316 may include one or more embedded contact signal pins 344 therein. As shown, the contact signal pins 344 may be positioned within the second arrest location 321. In other embodiments, the contact signal pins 344 may be positioned within the first arrest location 320, or within both the first and second arrest locations 320, 321. In the case contact signal pins 344 are located in both the first and second arrest locations 320 and 321, two distinct on/off states could be registered in place of a single 'on' or 'off' state. For example, this may be accomplished using a live contact signal pin 344 in each of the first and second arrest locations 320, 321 on one side of the pump chamber 306, and a distinct contact signal pin in corresponding arrest locations on an opposite side of the pump chamber 306.

During use of the pump 300, the contact signal pins 344 may not be in contact with the detent engagement members 318 when the pump chamber 306 is in a first position. When the pump chamber 306 moves away from a reservoir wall 312 of a fluid reservoir 304 and into a second position within the second arrest location 321, the contact signal pins 344 come into contact with the detent engagement members 318. A closed circuit is then formed between the contact signal pins 344 and the detent engagement members 318, causing a signal to be delivered to a processor or control logic/circuitry (not shown). For example, the signal obtained by actuating the closed-circuit switch may be an indicator of the status or position of the pump chamber 306. The information obtained by the switch about the position of the pump chamber 306 can be used, for example, to ensure that the pump 300 is drawing in or expelling fluid appropriately.

Figure 9:
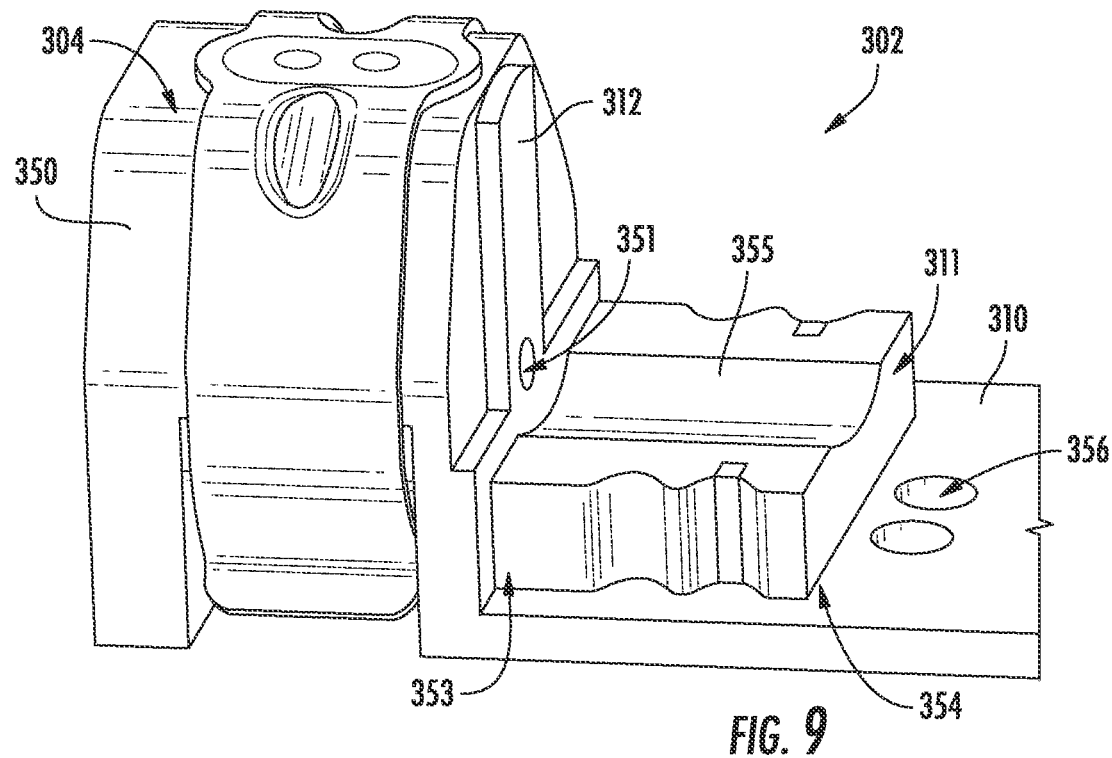
FIG. 9 illustrates a perspective view of an example pump housing according to embodiments of the present disclosure.

Turning now to FIG. 9, the pump housing 302 of the pump 300 according to embodiments of the present disclosure will be described in greater detail. As shown, the pump housing 302 may include the base 310 and the chassis 311 extending from the base 310 for retaining the pump chamber 306 (FIGS. 7-8). The pump housing 302 may further include a reservoir housing 350 defining or containing the fluid reservoir 304, wherein the fluid reservoir contains a fluid drug therein. The reservoir wall 312 may extend along an exterior of the reservoir housing 350, the reservoir wall 312 including a fluid opening 351 formed therethrough. In some embodiments, a needle (not shown) may extend through the fluid opening 351 to draw the fluid drug into the pump chamber 306.

In other embodiments, a piston rod of the piston 308 may extend into the fluid opening 351, initially blocking the fluid drug from being released from the fluid reservoir 304. When the piston rod is withdrawn from the reservoir housing 350, e.g., axially away from the reservoir wall 312, the fluid drug may be released from the fluid reservoir 304 and into the pump chamber 306. In some embodiments, movement of the piston rod can create a vacuum within a portion of the pump chamber 306, such as within a fluid line. The vacuum can pull a portion of the fluid drug out of the fluid reservoir 304 and into the created space/volume within the pump chamber 306.

As further shown, the chassis 311 may include a first (proximal) end 353 and a second (distal) end 354. A trough 355 may be provided in the chassis 311 to support the pump chamber 306. During use, the pump chamber 306 may slide within the trough 355, between the first and second ends 353, 354. The base 310 of the pump housing 302 may further include one or more openings 356 for receiving one or more contact members (not shown).

Figure 10:
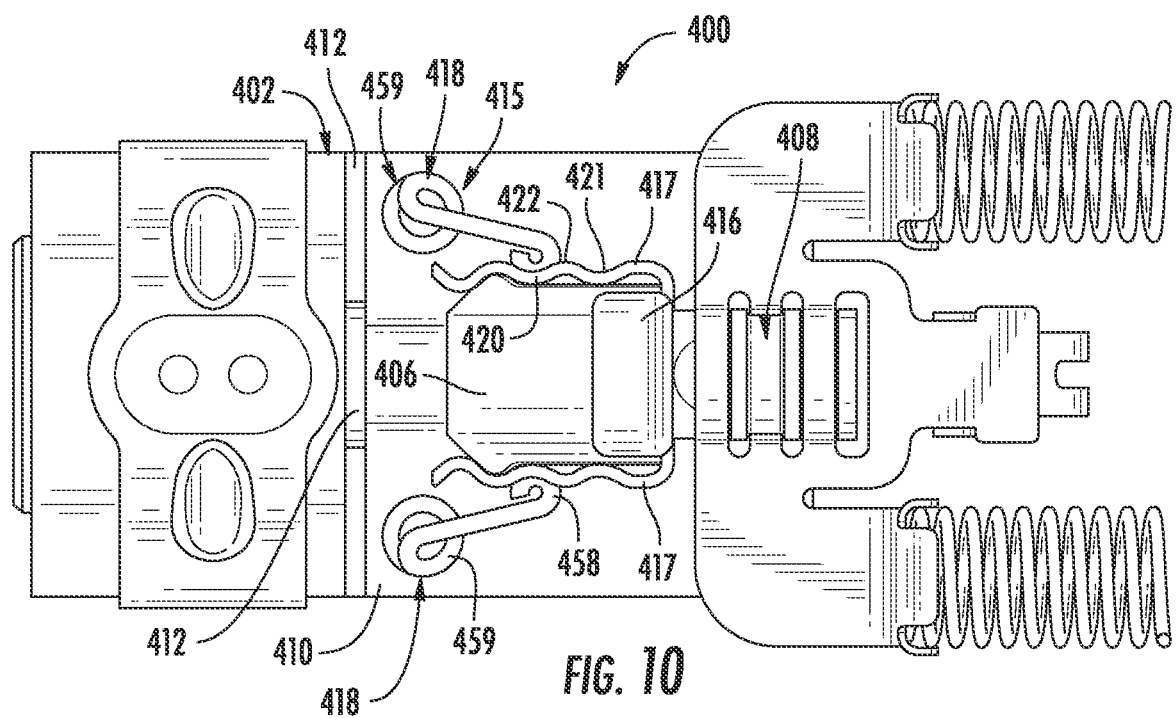
FIG. 10 illustrates a top view of an example linear volume shuttle fluid pump according to embodiments of the present disclosure.
Figure 11:
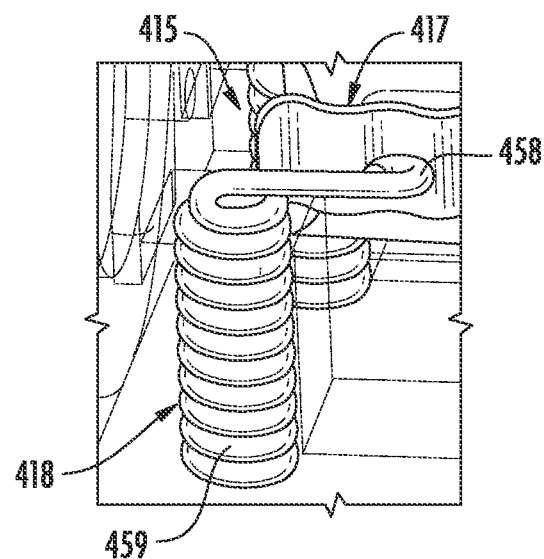
FIGS. 11-12 illustrate close-up views of a detent apparatus of the linear volume shuttle fluid pump depicted in FIG. 10 according to embodiments of the present disclosure.
Figure 12:
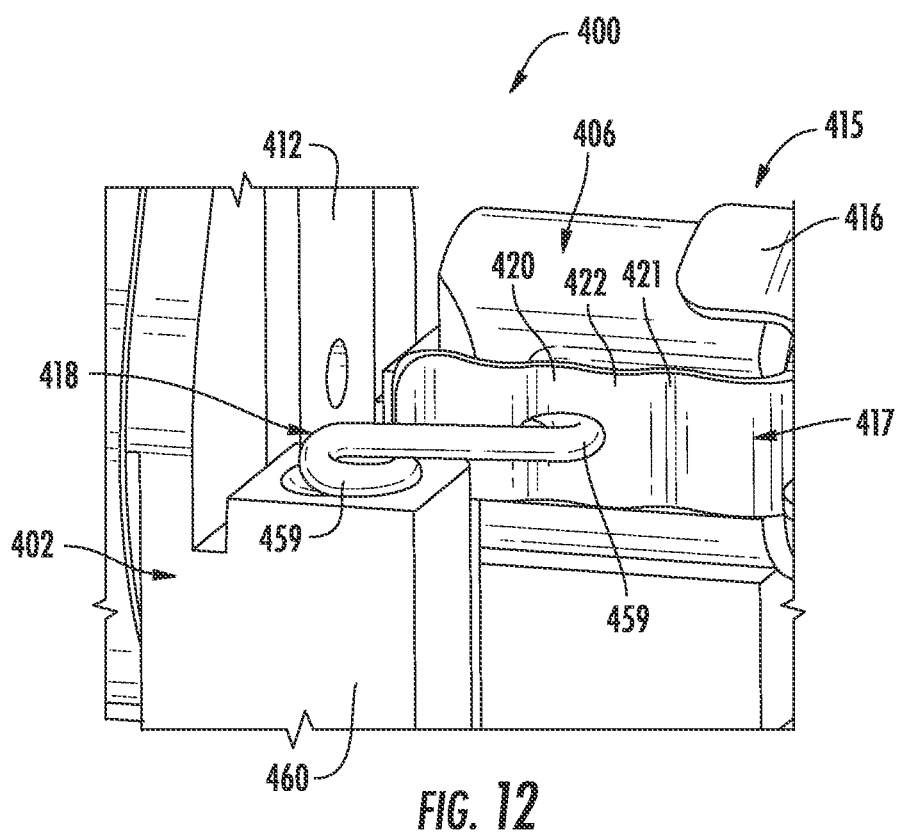

Referring to FIGS. 10-12, a pump 400 according to embodiments of the present disclosure will be described in greater detail. The pump 400 may be similar in many aspects to the pumps described above. As such, only certain aspects of the pump 400 may be described hereinafter for the sake of brevity. In this embodiment, the pump 400 may include a detent apparatus 415 coupled to a pump chamber 406. In some embodiments, the detent apparatus 415 may include a detent cap or body 416, one or more detent arms 417 extending from the detent body 416, and one or more detent engagement members 418. The detent body 416 may extend over and/or abut one end of the pump chamber 406. In some embodiments, the detent body 416 may further abut a piston 408, wherein an opening (not shown) of the detent body 416 may allow a rod of the piston 408 to pass therethrough.

The detent arms 417 may include a first arrest location 420 and a second arrest location 421. As shown, the first and second arrest locations 420, 421 may be defined by recesses or valleys disposed between one or more peaks 422. The first and second arrest locations 420, 421 may be curved to generally compliment the dimensions of the detent engagement members 418, which in this case, are torsion springs extending from a base 410 of the pump housing 402. More specifically, the detent engagement members 418 may include a contact section 458 connected to a helical section 459. In some embodiments, the helical section 459 may be housed or embedded within a spring housing 460 (FIG. 12), which may extend from, or be integrally formed with, the base 410. The first and second arrest locations 420, 421 allow discrete positioning of the pump chamber 406 and/or the piston 408 by adding additional frictional forces to restrict movement of the detent apparatus 415 prior to a desired time.

In the non-limiting embodiment depicted, the contact section 458 of the detent engagement member 418 may be retained in physical and/or electrical contact with the first arrest location 420 of the detent arm 417 when in a first position. In a second position, the contact section 458 of the detent engagement member 418 may be retained in physical and/or electrical contact with the second arrest location 421 of the detent arm 417. The detent engagement member 418 may change between the first position and second position as the pump chamber 406 moves away from a reservoir wall 412.

Figure 13:
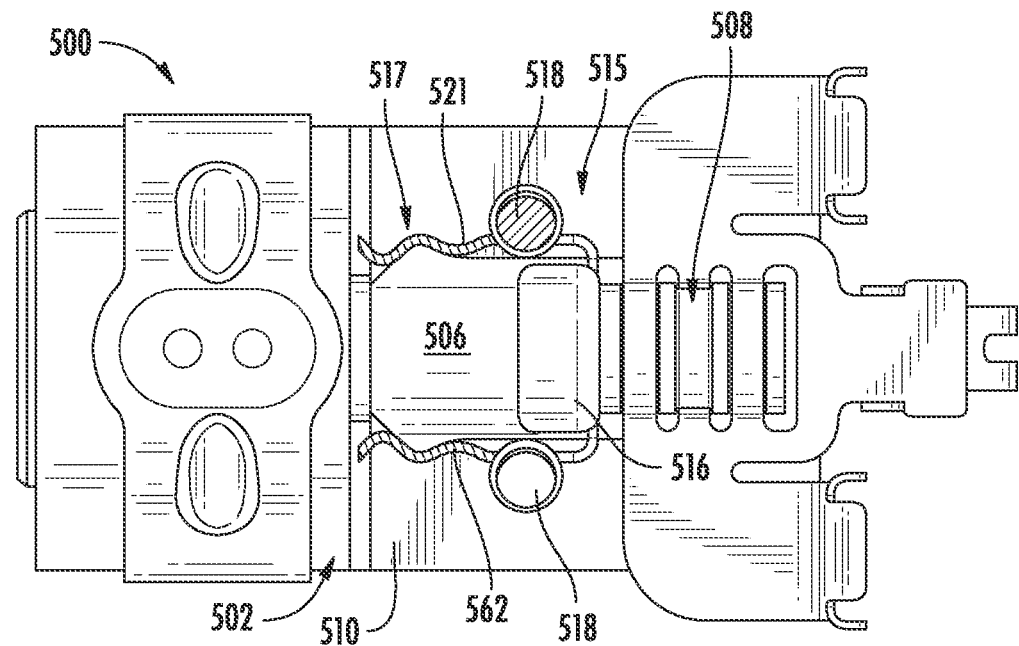
FIGS. 13-14 illustrate top views of an example linear volume shuttle fluid pump according to embodiments of the present disclosure.
Figure 14:
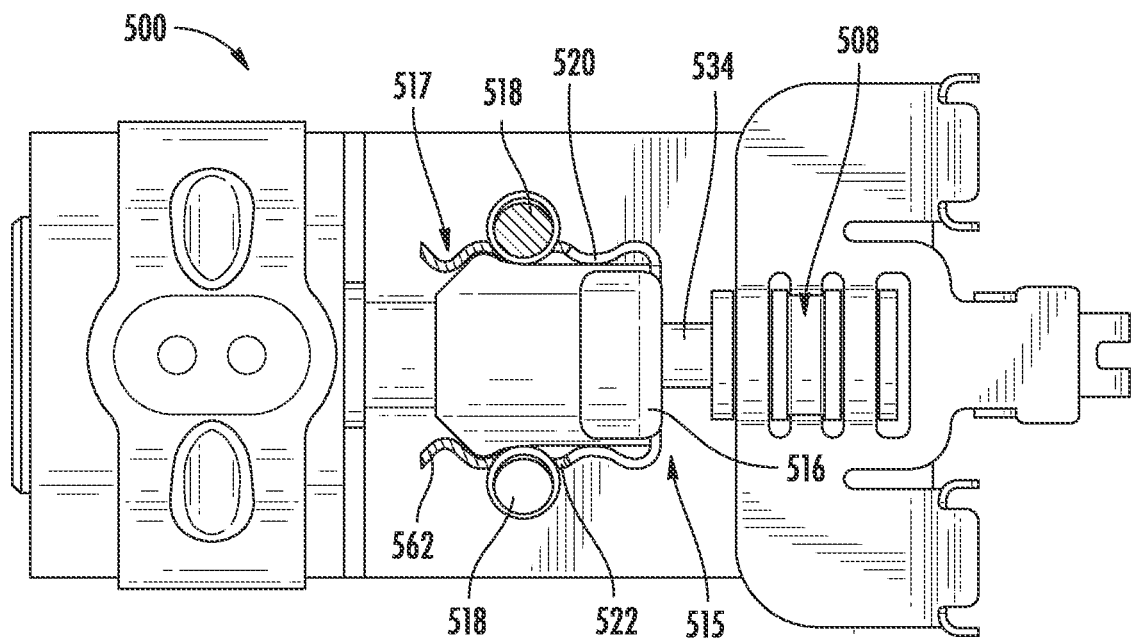

Referring to FIGS. 13-14, a pump 500 according to embodiments of the present disclosure will be described in greater detail. The pump 500 may be similar in many aspects to the pumps described above. As such, only certain aspects of the pump 500 may be described hereinafter for the sake of brevity. In this embodiment, the pump 500 may include a detent apparatus 515 coupled to a pump chamber 506. In some embodiments, the detent apparatus 515 may include a detent cap or body 516, one or more detent arms 517 extending from the detent body 516, and one or more detent engagement members 518. The detent body 516 may extend over and/or abut one end of the pump chamber 506. In some embodiments, the detent body 516 may further abut a piston 508, wherein an opening (not shown) of the detent body 516 may allow a rod 534 (FIG. 14) of the piston 508 to pass therethrough.

The detent arms 517 may include a first arrest location 520 and a second arrest location 521. As shown, the first and second arrest locations 520, 521 may be defined by recesses or valleys disposed between one or more peaks 522. The first and second arrest locations 520, 521 may be curved to generally compliment the dimensions of the detent engagement member 518, which in this case, may be a helical spring extending from a base 510 of the pump housing 502. The first and second arrest locations 520, 521 allow discrete positioning of the pump chamber 506 and/or the piston 508 by adding additional frictional forces to restrict movement of the detent apparatus 515 prior to a desired time.

In this embodiment, one or more of the detent engagement members 518 may include an insulative coating 562 formed thereon. As shown, the insulative coating 562 may be formed along just a portion of the detent arms such that the first arrest location 520 remains uncovered by the insulative coating 562. During use, as the pump chamber 506 and the detent apparatus 515 move away from a fluid reservoir 504, the detent arms 517 are repositioned relative to the detent engagement members 518 from the first arrest location 520 to the second arrest location 521, thus terminating electrical contact between the detent engagement members 518 and detent arms 517 due to the presence of the insulative coating 562. In other embodiments, the first arrest location 520 may be covered by the insulative coating 562, while the second arrest location 521 is uncovered by the insulative coating 562. As such, movement from the first arrest location 520 to the second arrest location 521 by the detent engagement members 518 may cause a closed circuit to be formed between the detent engagement members 518 and detent arms 517. A signal representing the closed/open circuit connection between the detent engagement members 518 and detent arms 517 may be used to determine a position of the pump chamber 506 and/or the piston 508.

Figure 15:
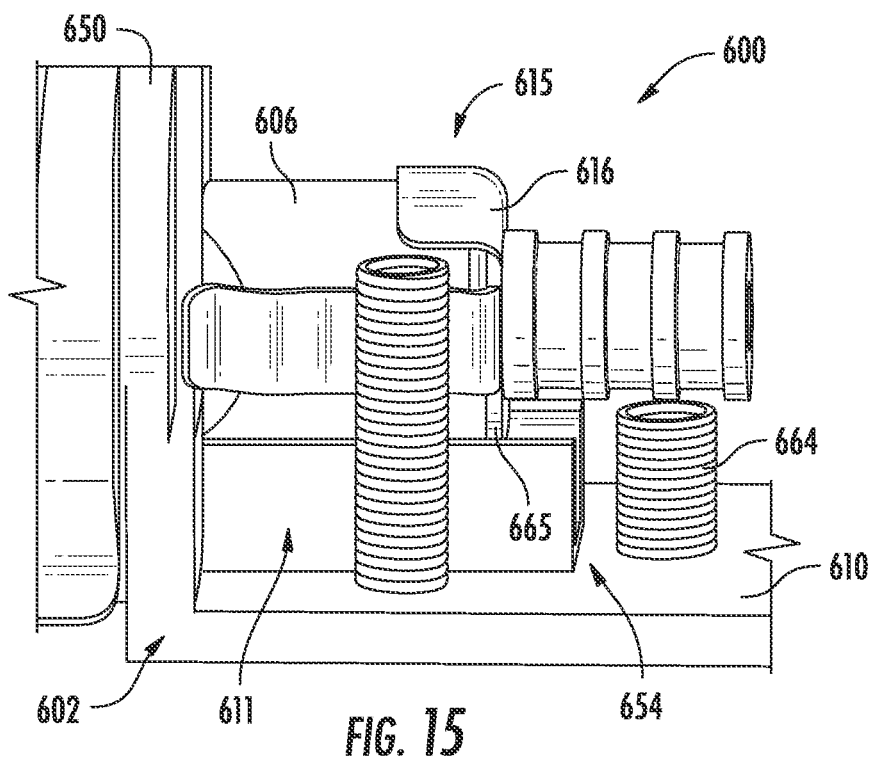
FIGS. 15-16 illustrate perspective views of an example linear volume shuttle fluid pump according to embodiments of the present disclosure.
Figure 16:
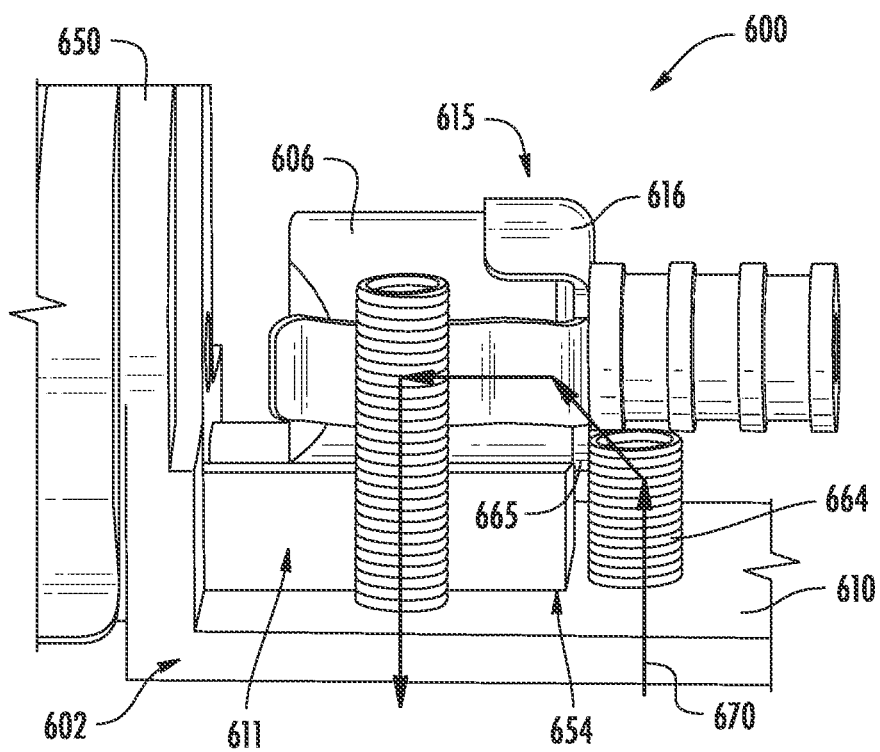

Referring to FIGS. 15-16, a pump 600 according to embodiments of the present disclosure will be described in greater detail. The pump 600 may be similar in many aspects to the pumps described above. As such, only certain aspects of the pump 600 may be described hereinafter for the sake of brevity.

As shown, the pump 600 may include one or more contact members 664, such as helical springs, extending from a base 610 of a pump housing 602. The contact member(s) 664 may form a closed circuit when contact is made with a perimeter 665 of a detent body 616 of a detent apparatus 615. For example, when a pump chamber 606 is in a first position adjacent a reservoir housing 650, as shown in FIG. 15, an open circuit is present. As the pump chamber 606 and the detent apparatus 615 are moved towards a distal end 654 of a chassis 611, the perimeter 665 of the detent body 616 makes electrical and mechanical contact with the contact member(s) 664 to form a closed circuit 670, as shown by a series of connected arrows in FIG. 16. A signal representing the closed/open circuit connection between the detent body 616 and the contact member(s) 664 may be used to determine a position of the pump chamber 606 and/or a piston 608.

In FIGS. 17-20, a pump 700 according to embodiments of the present disclosure will be described in greater detail. The pump 700 may be similar in many aspects to the pumps described above. As such, only certain aspects of the pump 700 may be described hereinafter for the sake of brevity.

As shown, the pump 700 may include one or more contact members 764, such as helical springs, extending from a base 710 of a pump housing 702. The contact members 764 may form a closed circuit when contact is made with a contact 767 of a detent body 716 of a detent apparatus 715. In this embodiment, the contact 767 may be an L-shaped contact extending from the detent body 716. As best demonstrated in FIGS. 19-20, the contact 767 may include a set of curled sides 768 operable to electrically and mechanically engage the contact members 764. For example, the contact 767 may extend between each of the contact members 764, deflecting the contact members 764 outwardly from a central axis (not shown) extending through an opening 769 (FIG. 19) of the detent body 716. It will be appreciated that the specific geometry and configuration of the contact 767 are non-limiting.

Figure 17:
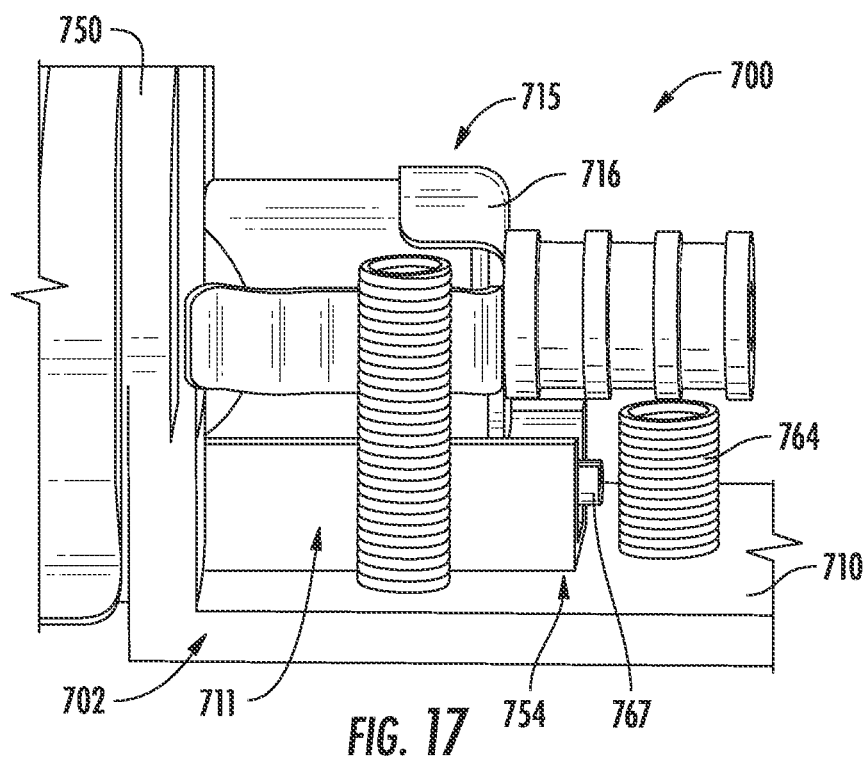
FIGS. 17-18 illustrate perspective views of an example linear volume shuttle fluid pump according to embodiments of the present disclosure.
Figure 18:
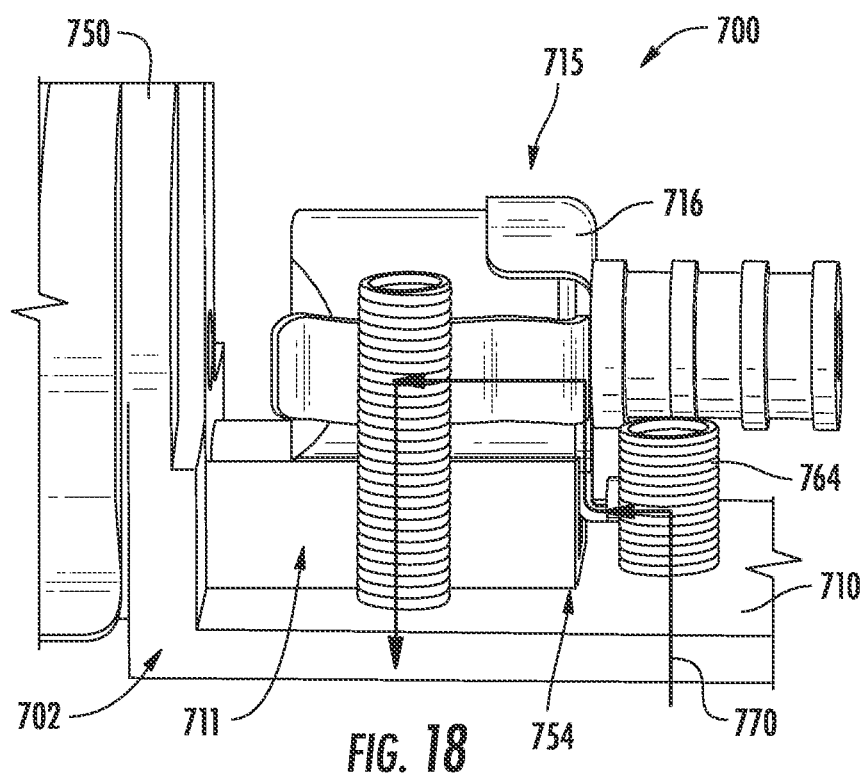
Figure 19:
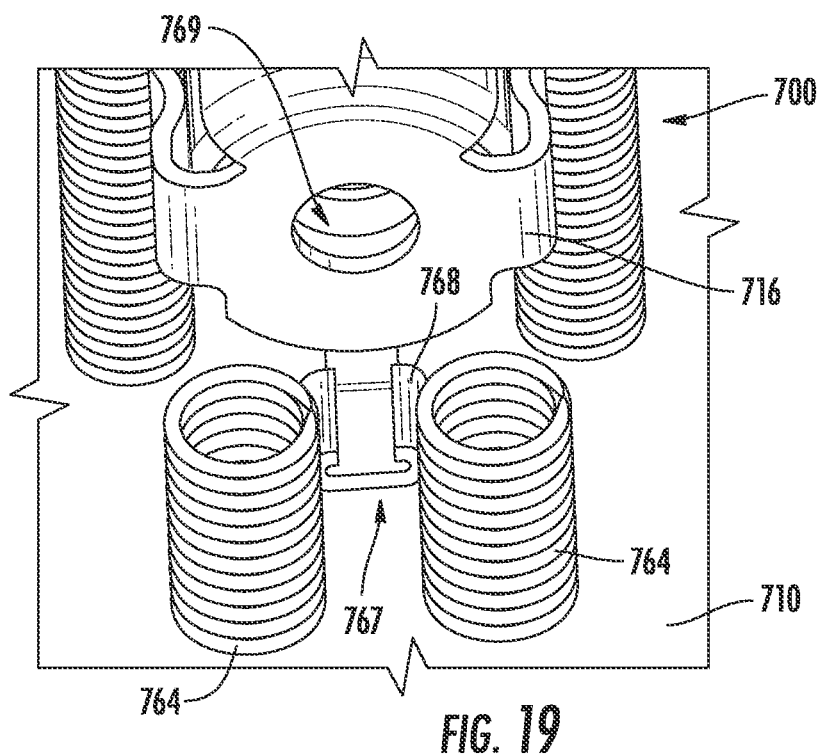
FIGS. 19-20 illustrate perspective views of a contact of the linear volume shuttle fluid pump depicted in FIGS. 17-18 according to embodiments of the present disclosure.
Figure 20:
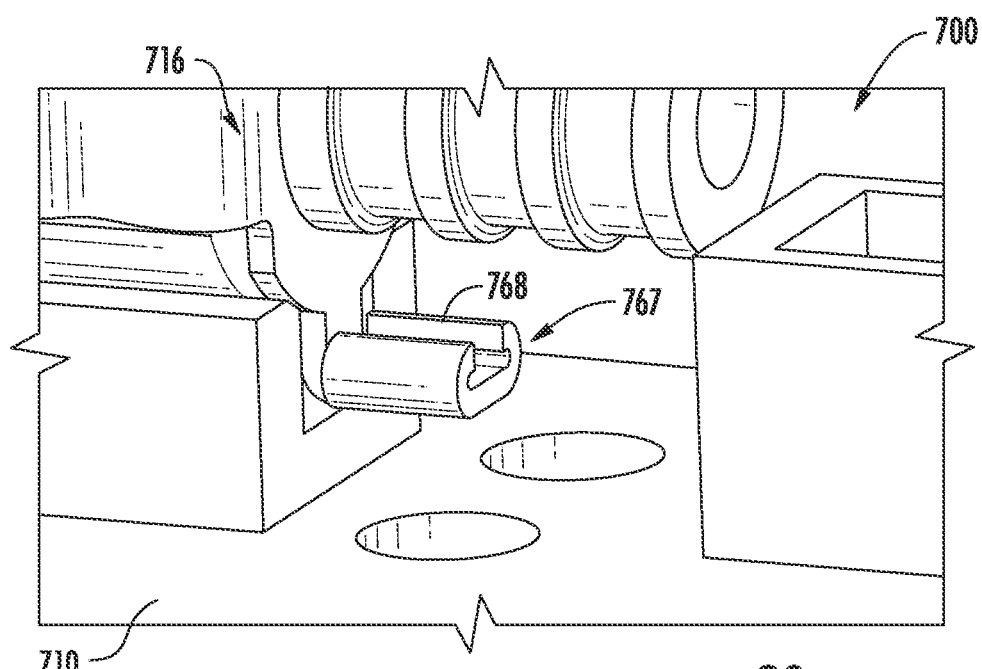

During use, when a pump chamber 706 is in a first position adjacent a reservoir housing 750, as shown in FIG. 17, an open circuit exists. As the pump chamber 706 and the detent apparatus 715 move towards a distal end 754 of a chassis 711, the contact 767 makes electrical and mechanical contact with the contact members 764 to form a closed circuit 770, as shown by a series of connected arrows in FIG. 18. A signal representing the closed/open circuit connection between the contact 767 and the contact members 764 may be used to determine a position of the pump chamber 706 and/or a piston 708.

Figure 21:
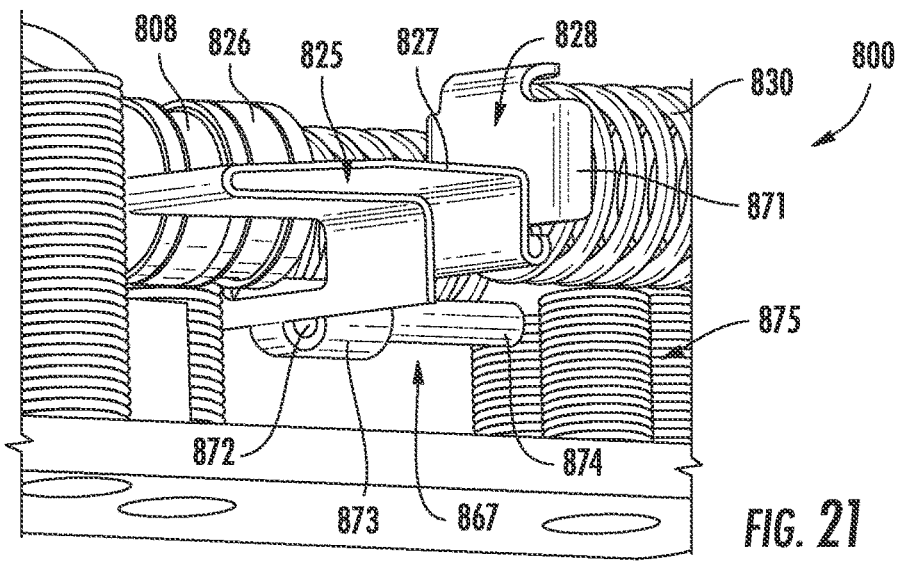
FIGS. 21-22 illustrate perspective views of an example linear volume shuttle fluid pump according to embodiments of the present disclosure.
Figure 22:
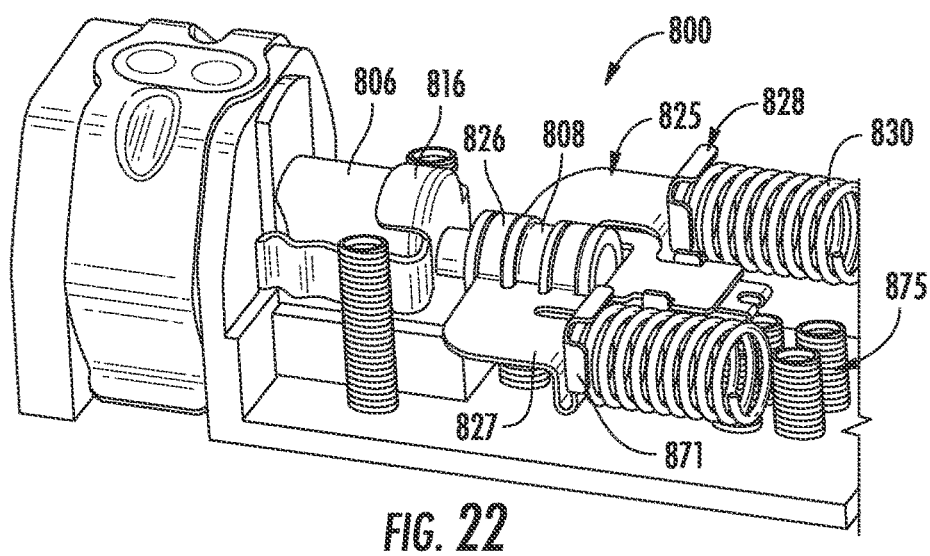
Figure 23:
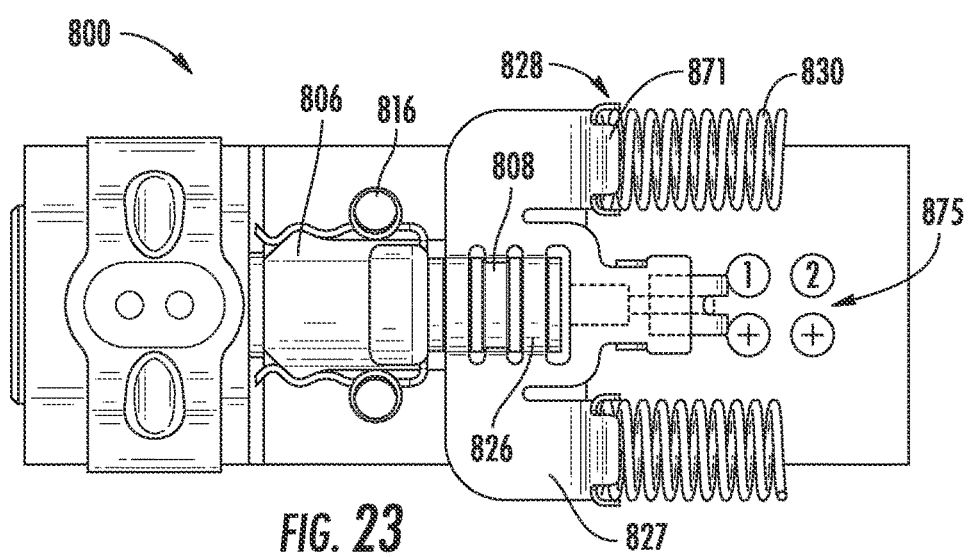
FIG. 23 illustrates a top view of the linear volume shuttle fluid pump depicted in FIGS. 21-22 according to embodiments of the present disclosure.

Referring to FIGS. 21-23, a pump 800 according to embodiments of the present disclosure will be described in greater detail. The pump 800 may be similar in many aspects to the pumps described above. As such, only certain aspects of the pump 800 may be described hereinafter for the sake of brevity. In this embodiment, the pump 800 may include a piston grip 825 coupled to a piston 808. The piston grip 825 may include one or more grip components 826 engaged with an exterior of the piston 808. During operation, movement of the piston grip 825 causes the piston 808 to move axially relative to a pump chamber 806 to control receipt and delivery of a liquid drug within the pump chamber 806.

In some embodiments, the piston grip 825 includes a grip body 827 extending on opposite sides of the piston 808. The grip body 827 may include one or more spring footers 828 extending therefrom. As shown, each spring footer 828 may include one or more tabs 871 to engage and retain therein a side spring 830. In this embodiment, the side springs 830 may be disposed on opposite sides of the piston 808, parallel to a central axis (not shown) extending through the piston 808, the pump chamber 806, and a detent body 816. The side springs 830 provide a spring force to bias the piston grip 825, and thus the piston 808, towards the pump chamber 806.

In this embodiment, the piston grip 825 may further include a contact 867 coupled thereto. Although non-limiting, the contact 867 may be an insulated dowel pin disposed along an underside of the grip body 827. For example, the contact 867 may be an electrically conductive cylinder generally extending parallel to the central axis. In some embodiments, the contact 867 may include a first end 872 retained within a clamp 873 of the piston grip 825, and a second, free end 874 opposite the first end 872. The free end 874 is operable to engage one or more piston position contact members 875, as will be described below.

Figure 24:
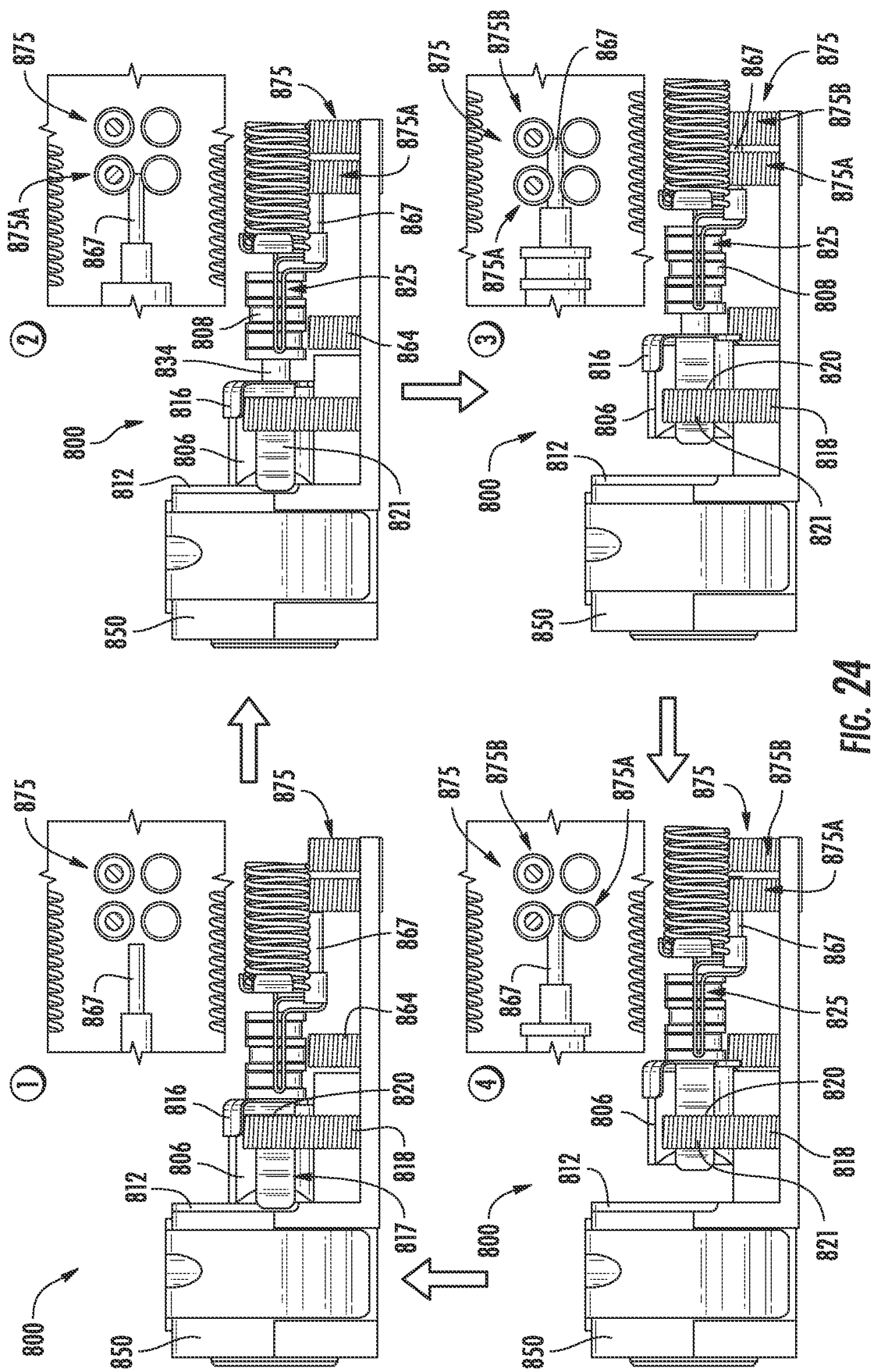
FIG. 24 illustrates a sequence for operating an example linear volume shuttle fluid pump according to embodiments of the present disclosure.

Turning now to FIG. 24, operation of the pump 800 according to embodiments of the present disclosure will be described in greater detail. As shown, for each state of the pump 800, both a side view of the pump 800 and a close-up, top view of the contact 867 and the piston position contact members 875 are depicted. In an initial stage (1), the pump chamber 806 may be directly adjacent and/or in abutment with a reservoir wall 812 of a reservoir housing 850. Additionally, an engagement member 818 may be retained in direct physical contact with a first arrest location 820 of a detent arm 817 when the pump chamber 806 is in the initial stage (1). As shown, no contact is made, for example, between the detent body 816 and the contact members 864, or between the contact 867 and the piston position contact members 875.

Next, at a second stage (2), the piston 808 may move axially away from the pump chamber 806 to draw a liquid drug into the pump chamber 806. More specifically, a piston rod 834 of the piston 808 may be withdrawn axially through the pump chamber 806 to release a fluid drug from the reservoir housing 850. As shown, the piston grip 825 and the contact 867 may also move axially away from the pump chamber 806, causing the contact 867 to engage a first pair 875A of the piston position contact members 875. A signal may be delivered from the piston position contact members 875 to indicate a position of the contact 867 and thus the piston 808. An open circuit between the detent body 816 and the contact members 864 may provide an indication of a position of the pump chamber 806.

Next, at a third stage (3), the pump chamber 806 and the piston 808 may move axially away from the reservoir housing 850 to bring a needle (not shown) of the pump chamber 806 into a fluid output position. As shown, the piston grip 825 and the contact 867 may engage the first pair 875A and a second pair 875B of the piston position contact members 875. A signal may be delivered from the piston position contact members 875 to indicate a position of the contact 867 and thus the piston 808. Furthermore, a closed circuit between the detent body 816 and the contact members 864 may also provide an indication of a position of the pump chamber 806. As shown, the detent engagement member 818 may be retained in direct physical contact with a second arrest location 821 of the detent arm 817.

Next, at a fourth stage (4), the piston 808 may move axially towards the pump chamber 806 to expel the fluid drug from the pump chamber 806. As shown, the piston grip 825 and the contact 867 may engage only the first pair 875A of the piston position contact members 875. A signal may be delivered from the piston position contact members 875 to indicate a position of the contact 867 and thus the piston 808. Furthermore, the closed circuit between the detent body 816 and the contact members 864 may also provide an indication of a position of the pump chamber 806. As shown, the detent engagement member 818 may remain in direct physical contact with a second arrest location 821 of the detent arm 817 at the fourth stage.

Figure 25:
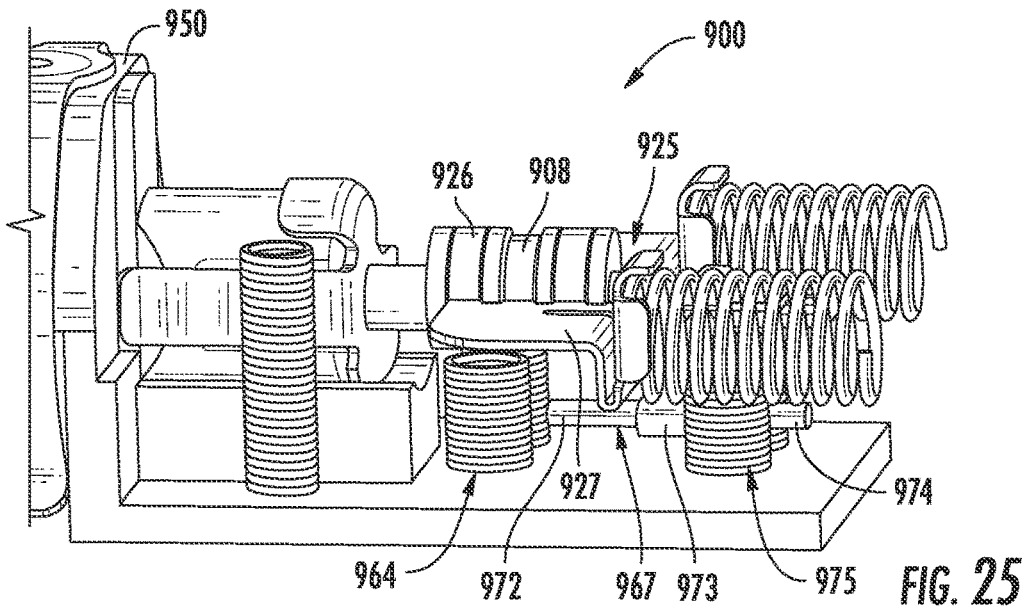
FIGS. 25-26 illustrate perspective views of an example linear volume shuttle fluid pump according to embodiments of the present disclosure.
Figure 26:
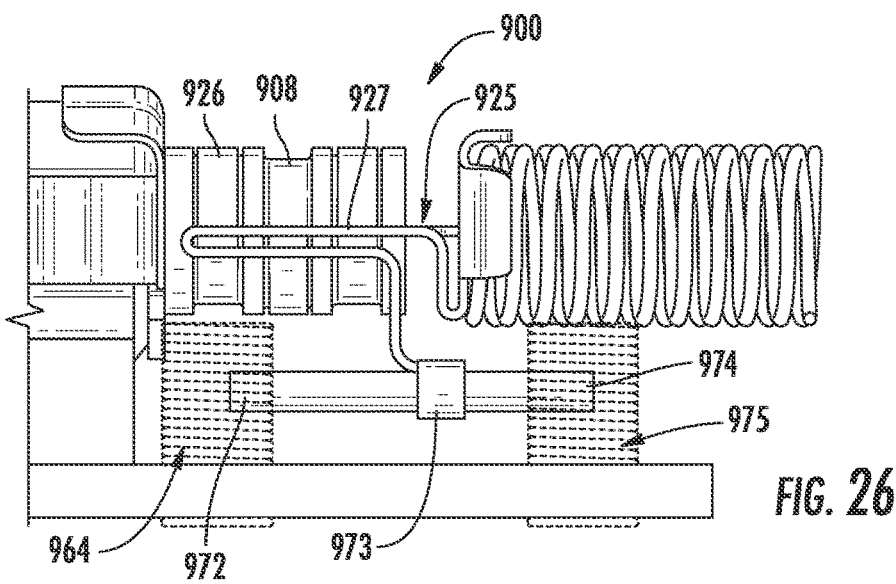
Figure 27:
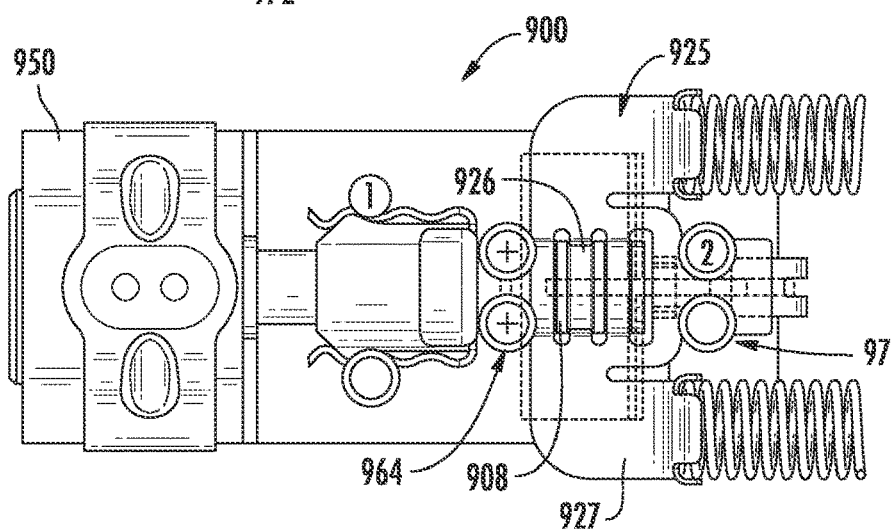
FIG. 27 illustrates a top view of the linear volume shuttle fluid pump depicted in FIGS. 25-26 according to embodiments of the present disclosure.

Referring now to FIGS. 25-27, a pump 900 according to embodiments of the present disclosure will be described in greater detail. The pump 900 may be similar in many aspects to the pumps described above. As such, only certain aspects of the pump 900 may be described hereinafter for the sake of brevity. In this embodiment, the pump 900 may include a piston grip 925 coupled to a piston 908. The piston grip 925 may include one or more grip components 926 engaged with an exterior of the piston 908. During operation, movement of the piston grip 925 causes the piston 908 to move axially relative to the pump chamber 906 and to a reservoir housing 950 containing a fluid drug.

In some embodiments, the piston grip 925 includes a grip body 927 extending on opposite sides of the piston 908, and a contact 967 coupled thereto. Although non-limiting, the contact 967 may be a dowel pin disposed along an underside of the grip body 927. For example, the contact 967 may be an electrically conductive cylinder generally extending parallel to the central axis. The contact 967 may include a first end 972 proximate contact members 964 and a second end 974 proximate one or more piston position contact members 975. As shown, the contact 967 may be joined to the grip body 927 by one or more clamps 973.

Figure 28:
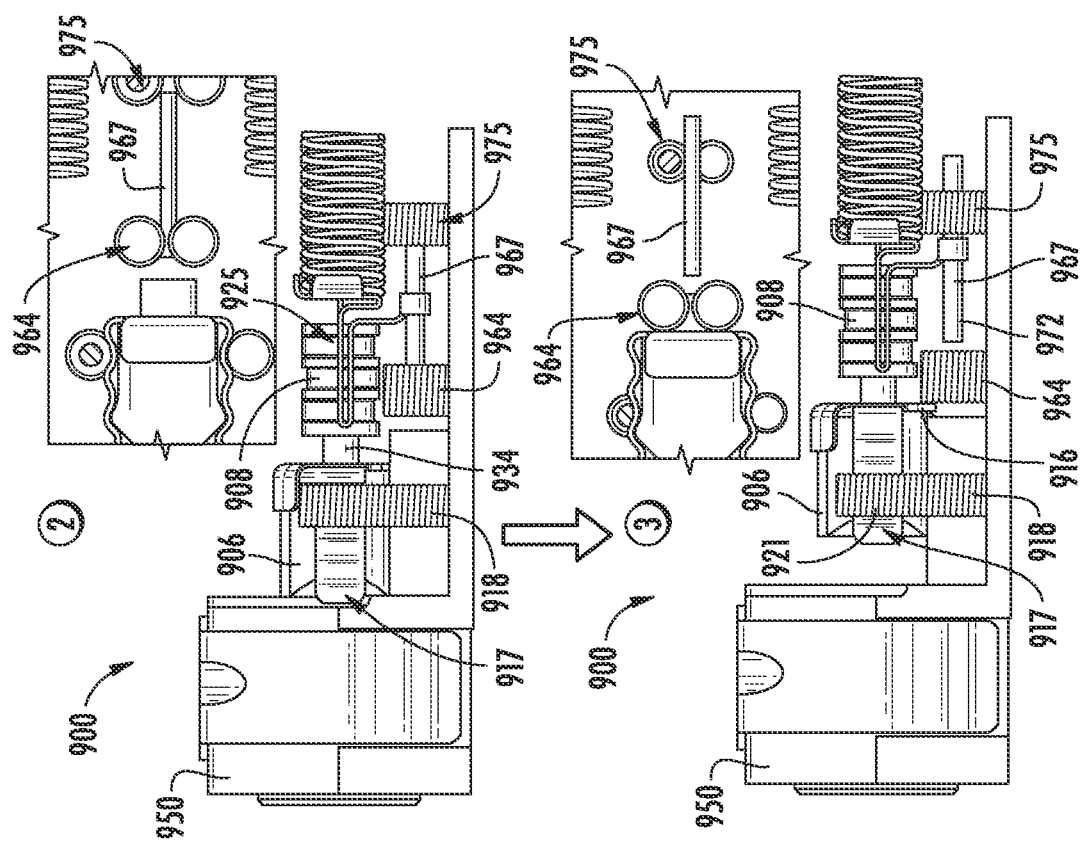
FIG. 28 illustrates a sequence for operating an example linear volume shuttle fluid pump according to embodiments of the present disclosure.
Figure 28:
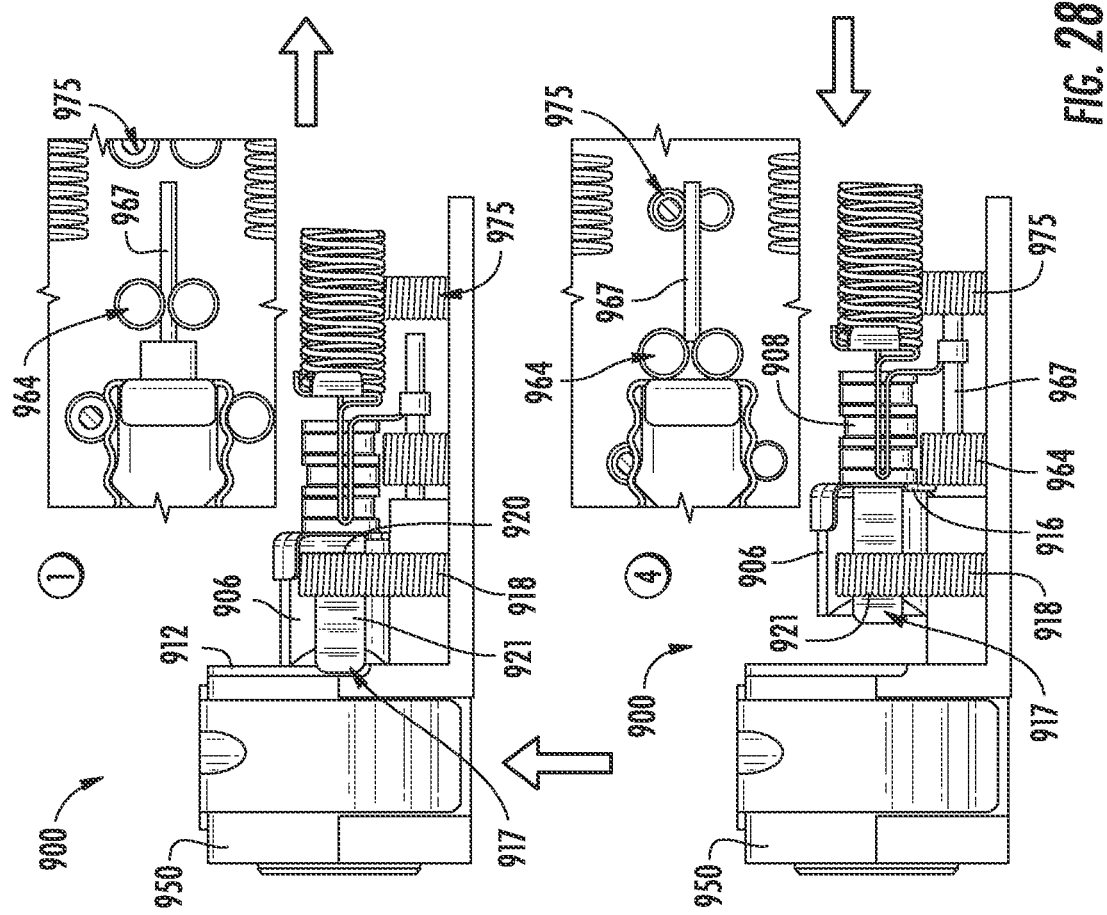

Turning now to FIG. 28, operation of the pump 900 according to embodiments of the present disclosure will be described in greater detail. As shown, for each state of the pump 900, both a side view of the pump 900 and a close-up, top view of the contact 967, the contact members 964, and the piston position contact members 975 are depicted. In an initial stage (1), the pump chamber 906 may be directly adjacent and/or in abutment with a reservoir wall 912 of a reservoir housing 950. Additionally, an engagement member 918 may be retained in direct physical contact with a first arrest location 920 of a detent arm 917 when the pump chamber 906 is in the initial stage (1). As shown, the contact 967 may be in direct physical and electrical contact with the contact members 964, but not the piston position contact members 975.

Next, at a second stage (2), the piston 908 may move axially away from the pump chamber 906 to draw a liquid drug into the pump chamber 906. More specifically, a piston rod 934 of the piston 908 may be withdrawn axially through the pump chamber 906 to release a fluid drug from the reservoir housing 950. As shown, the piston grip 925 and the contact 967 may also move axially away from the pump chamber 906, causing the contact 967 to engage the piston position contact members 975. A signal may be delivered from the piston position contact members 975 and the contact members 964 to indicate a position of the contact 967 and thus the piston 908.

Next, at a third stage (3), the pump chamber 906 and the piston 908 may move axially away from the reservoir housing 950 to bring a needle (not shown) of the pump chamber 906 into a fluid output position. As shown, the piston grip 925 and the contact 967 may continue to move axially away from the reservoir housing 950, causing the first end 972 of the contact 967 to break contact with the contact members 964. One or more signals may be delivered from the piston position contact members 975 and the contact members 964 to indicate a position of the contact 967 and thus the piston 908. In some embodiments, a closed circuit between the detent body 916 and the contact members 964 may also provide an indication of a position of the pump chamber 906. As shown, the detent engagement member 918 may be retained in direct physical contact with a second arrest location 921 of the detent arm 917.

Next, at a fourth stage (4), the piston 908 may move axially towards the pump chamber 906 to expel the fluid drug from the pump chamber 906. As shown, the contact 967 may again engage both the piston position contact members 975 and the contact members 964. A signal may be delivered from the piston position contact members 975 and the contact members 964 to indicate a position of the contact 967 and thus the piston 908. Furthermore, the closed circuit between the detent body 916 and the contact members 964 may also provide an indication of a position of the pump chamber 906. As shown, the detent engagement member 918 may remain in direct physical contact with a second arrest location 921 of the detent arm 917 at the fourth stage.

Figure 29:
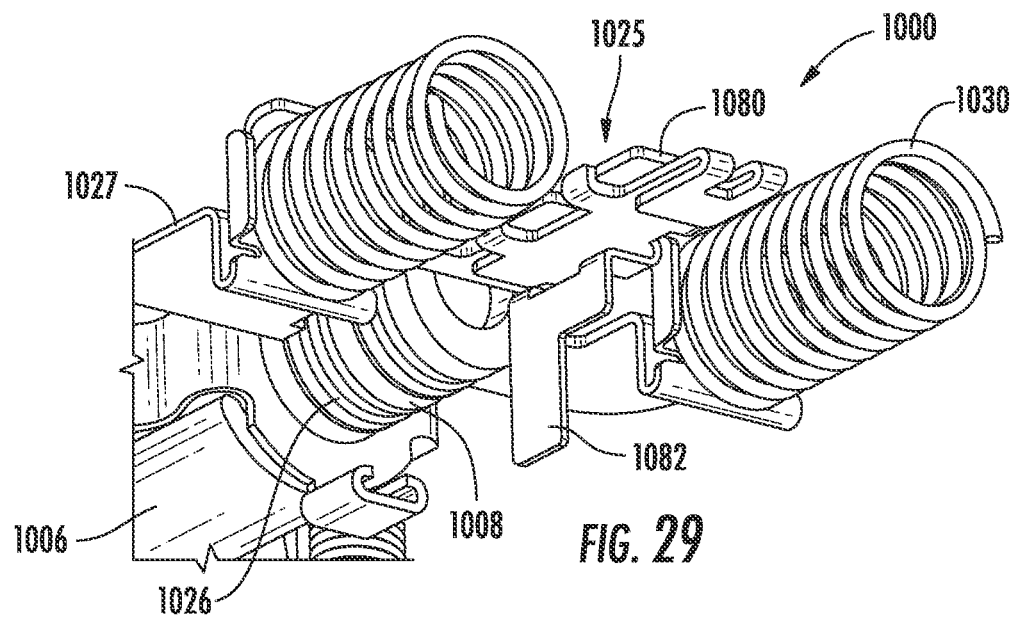
FIGS. 29-30 illustrate perspective views of an example linear volume shuttle fluid pump including an optical sensor according to embodiments of the present disclosure.
Figure 30:
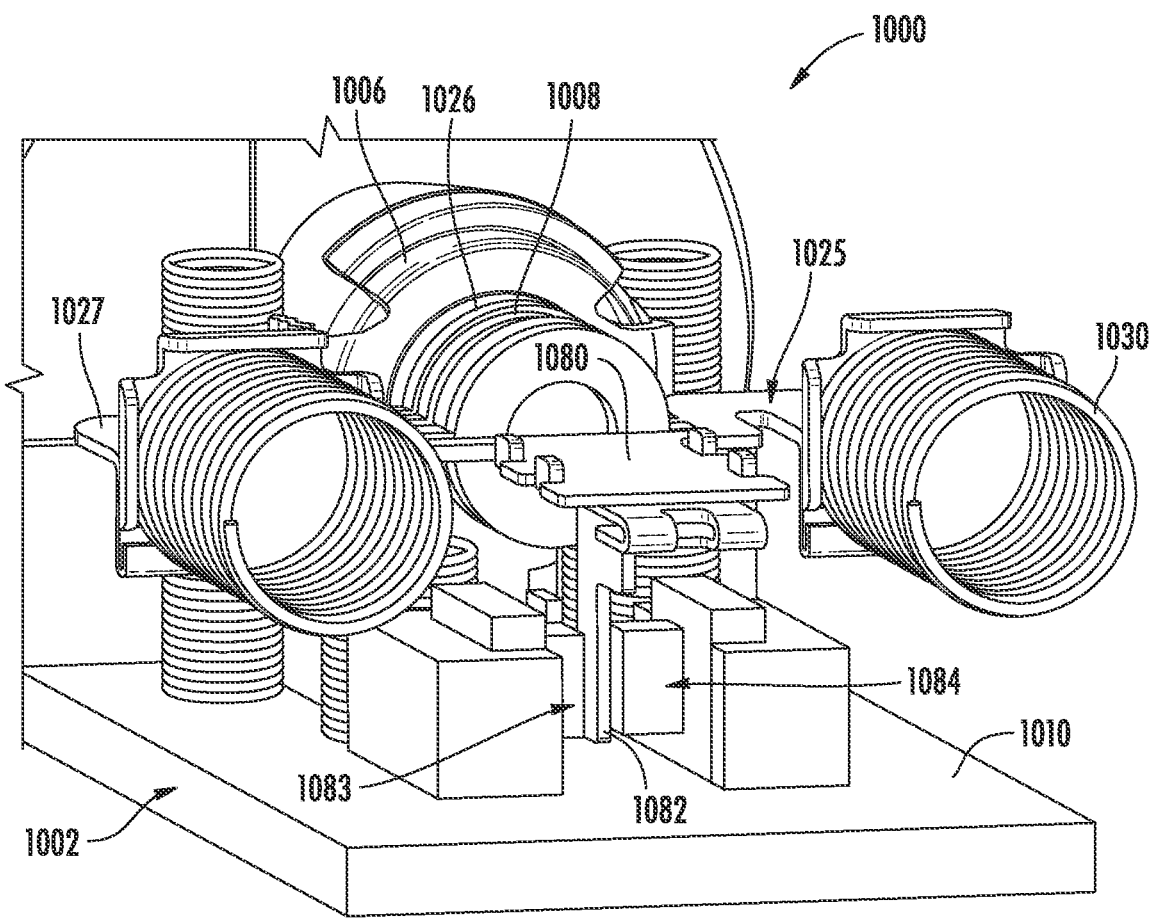

Turning now to FIGS. 29-30, a pump 1000 according to embodiments of the present disclosure will be described in greater detail. The pump 1000 may be similar in many aspects to the pumps described above. As such, only certain aspects of the pump 1000 may be described hereinafter for the sake of brevity. In this embodiment, the pump 1000 may include a piston grip 1025 coupled to a piston 1008. The piston grip 1025 may include one or more grip components 1026 engaged with an exterior of the piston 1008. During operation, the piston grip 1025 and the piston 1008 may move together, axially relative to a pump chamber 1006.

In some embodiments, the piston grip 1025 includes a grip body 1027 extending on opposite sides of the piston 1008. The grip body 1027 may further include a sensor plate 1080 extending between a pair of side springs 1030. A sensor arm 1082 may extend perpendicularly from the sensor plate 1080, wherein the sensor arm 1082 operates with an optical sensor 1085 to detect a position of the piston grip 1025 and thus the piston 1008. More specifically, as better shown in FIG. 30, the sensor arm 1082 may travel between a light source 1083 (e.g., LED) and a photodiode 1084. The light source 1083 and the photodiode 1084 may extend from a base 1010 of a housing 1002.

The photodiode 1084 is operable to detect light from the light source 1083. When the sensor arm 1082 is positioned between the light source 1083 and the photodiode 1084, the photodiode will not detect any light. When the sensor arm 1082 is not positioned between the light source 1083 and the photodiode 1084, the photodiode will detect the light output from the light source 1083. Based on the detection or non-detection of light, the position of the piston grip 1025 and thus the piston 1008 can be determined.

Figure 31:
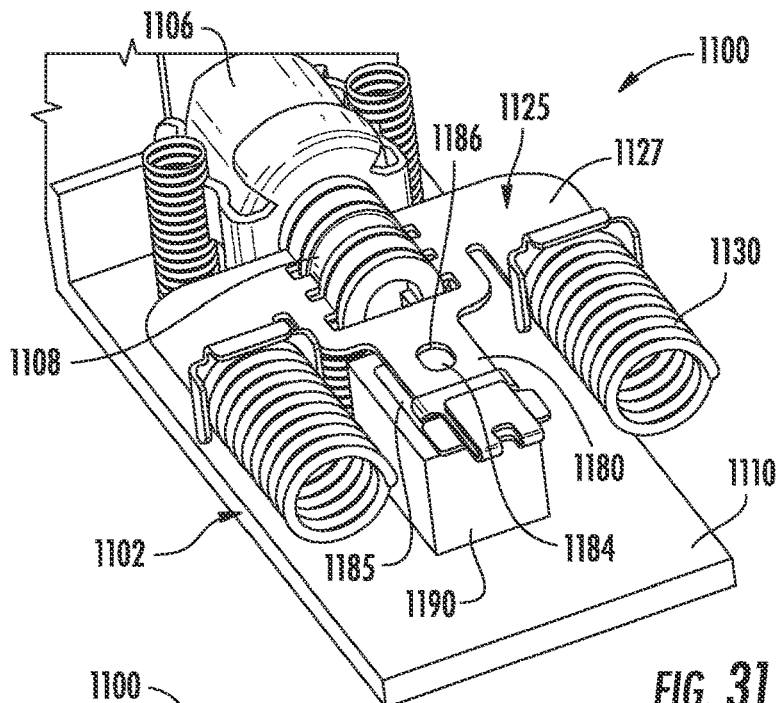
FIG. 31 illustrates a perspective view of an example linear volume shuttle fluid pump including an optical sensor according to embodiments of the present disclosure.
Figure 32:
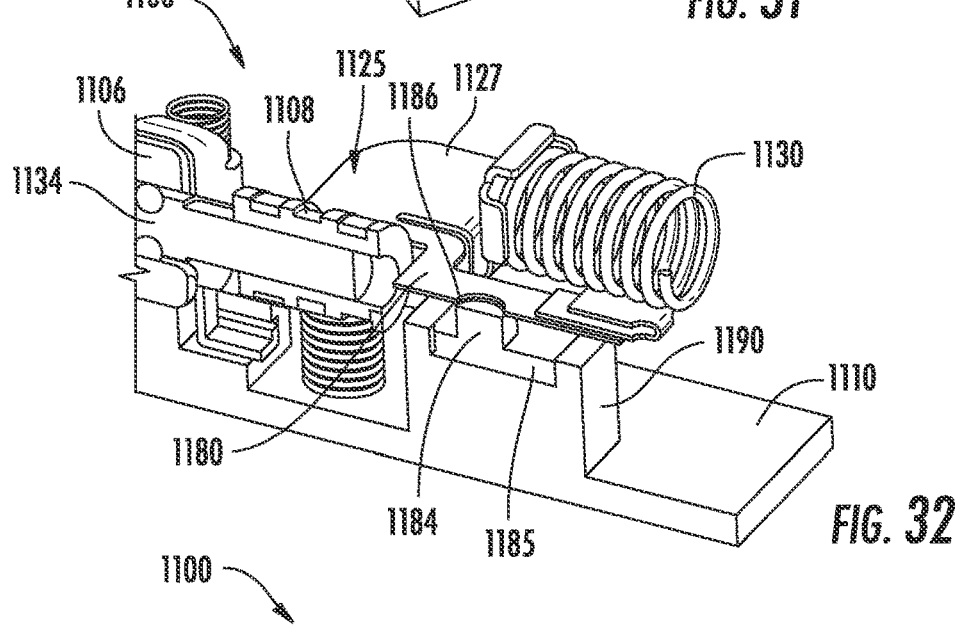
FIG. 32 illustrates a cross-sectional view of the linear volume shuttle fluid pump depicted in FIG. 31 according to embodiments of the present disclosure.
Figure 33:
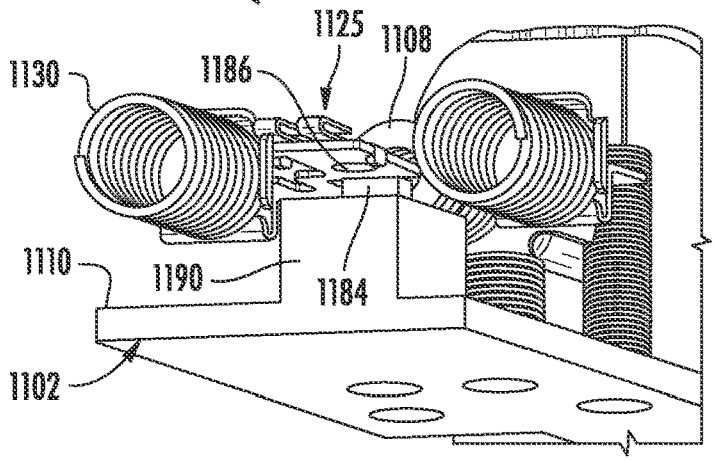
FIG. 33 illustrates a perspective view of the linear volume shuttle fluid pump depicted in FIG. 31 according to embodiments of the present disclosure.

Turning now to FIGS. 31-33, a pump 1100 according to embodiments of the present disclosure will be described in greater detail. The pump 1100 may be similar in many aspects to the pumps described above. As such, only certain aspects of the pump 1100 may be described hereinafter for the sake of brevity. In this embodiment, the pump 1100 may include a piston grip 1125 coupled to a piston 1108. During operation, movement of the piston grip 1125 causes the piston 1108 to move axially relative to a pump chamber 1106 and/or a piston rod 1134.

In some embodiments, the piston grip 1125 includes a grip body 1127 extending on opposite sides of the piston 1108. The grip body 1127 may further include a sensor plate 1180 extending between a pair of side springs 1130. As further shown, the sensor plate 1180 may positioned distal of the piston 1108. In this embodiment, the sensor plate 1180 may include an optical opening 1186 positioned above an optical sensor 1185. Light from a light source (not shown), may reach a photodiode 1184 of the optical sensor 1185 depending on a position of the sensor plate 1180. For example, when a solid portion 1187 of the sensor arm 1182 is positioned between the light source and the photodiode 1184, the photodiode will not detect any light. However, when the optical opening 1186 is positioned over the photodiode 1184, light from the light source is permitted to reach the photodiode 1184. Based on the detection or non-detection of light by the photodiode 1184, the position of the piston grip 1125 and thus the piston 1108 can be determined. In some embodiments, the optical sensor 1185 can be elevated to a position proximate the grip body 1127 by a sensor block 1190 extending from a base 1110 of a housing 1102 of the pump 1100. Embodiments herein are not limited in this context, however.

Figure 34:
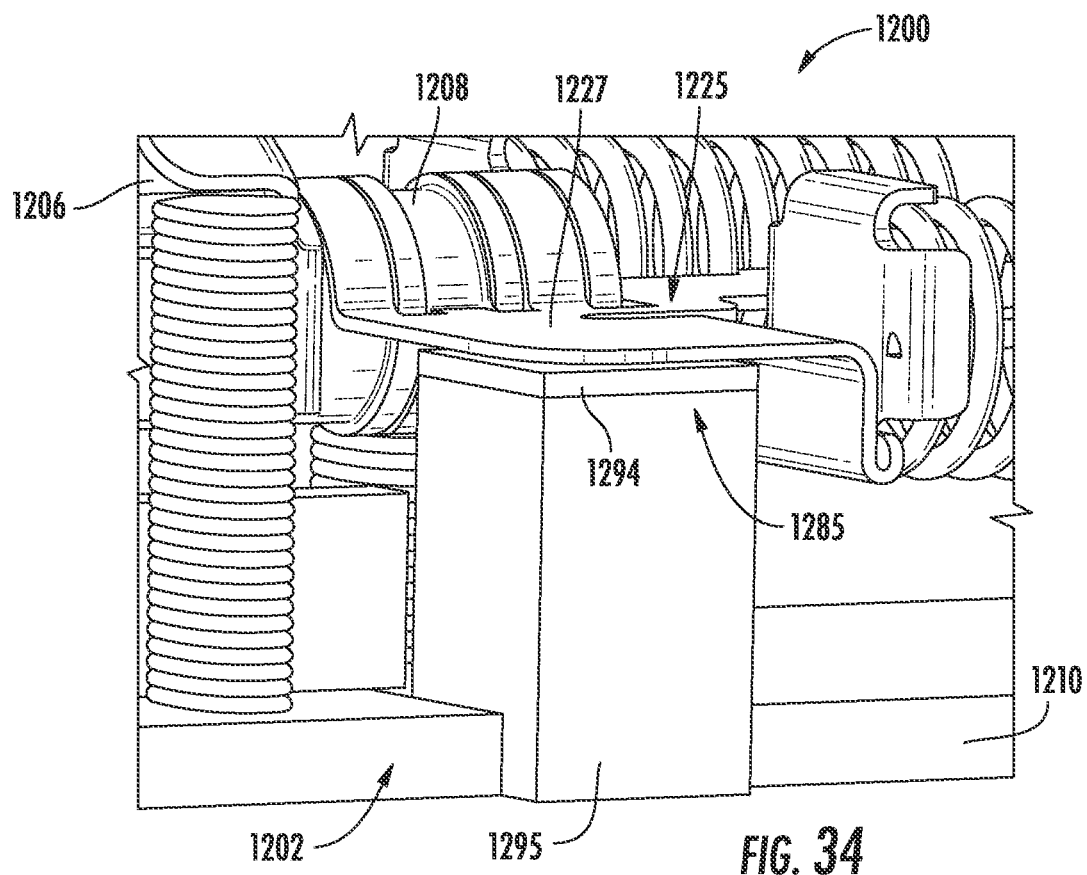
FIGS. 34-35 illustrate perspective views of an example linear volume shuttle fluid pump including a capacitive sensor according to embodiments of the present disclosure.
Figure 35:
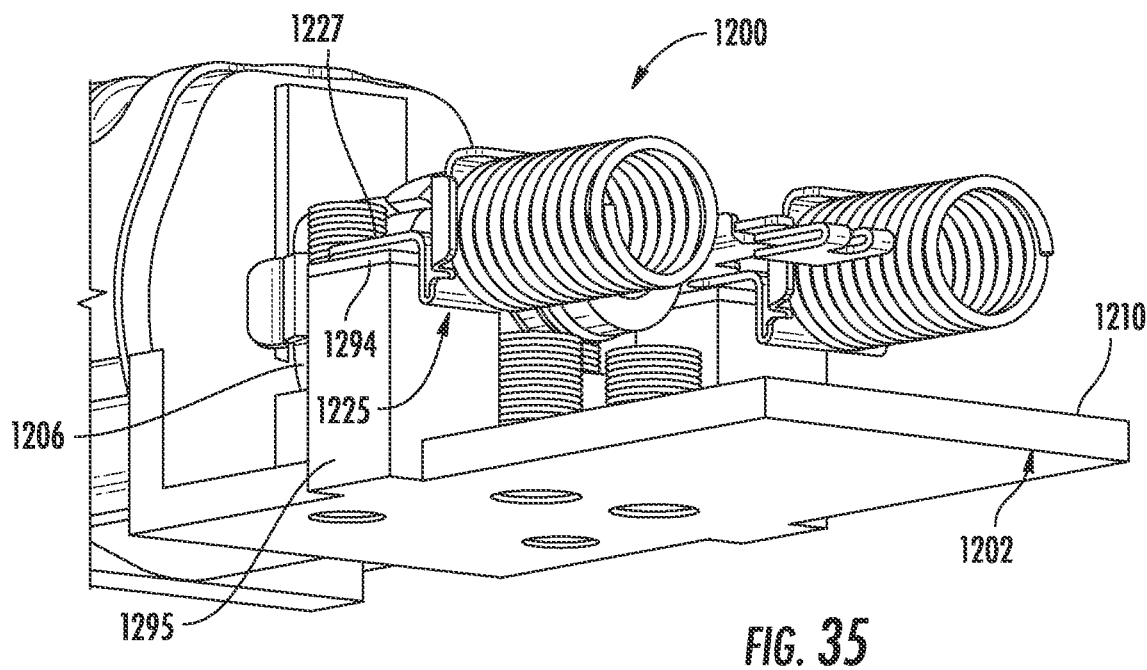

Turning now to FIGS. 34-35, a pump 1200 according to embodiments of the present disclosure will be described in greater detail. The pump 1200 may be similar in many aspects to the pumps described above. As such, only certain aspects of the pump 1200 may be described hereinafter for the sake of brevity. In this embodiment, the pump 1200 may include a piston grip 1225 coupled to a piston 1208. During operation, movement of the piston grip 1225 causes the piston 1208 to move axially relative to a pump chamber 1206.

In some embodiments, the piston grip 1225 includes a grip body 1227 extending on opposite sides of the piston 1208. The grip body 1227 may operate with a capacitive sensor 1285. For example, the capacitive sensor 1285 may include a capacitive plate 1294 mounted atop a capacitor block 1295 extending from a base 1210 of a housing 1202. During use, a temporary capacitor may be formed when grip body 1227, which is grounded, moves above the capacitive plate 1294. The capacitance can be measured, for example, by a component on a logic board (not shown) and can directly indicate the location of the piston grip 1215 and thus the piston 1208. This approach can offer multiple degrees of resolution between pump states since the capacitance measured by the capacitive sensor 1285 increases and decreases linearly with the motion of the grip body 1227 of the capacitive plate 1294.

In sum, the systems, apparatuses, and methods disclosed herein may be used to extract a portion of a liquid drug or other fluid from a reservoir. The pumps disclosed herein may be the linear shuttle pumps and/or and linear volume shuttle fluid pumps for providing a stored liquid drug to a user by, for example, extracting a liquid drug from a reservoir, temporarily storing the extracted liquid drug within the pump, and then expelling the liquid drug from the pump for delivery to the patient. Each of the disclosed pumps may be part of a wearable medical device such as, for example, a wearable insulin delivery device.

The foregoing discussion has been presented for purposes of illustration and description and is not intended to limit the disclosure to the form or forms disclosed herein. For example, various features of the disclosure may be grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The use of "including," "comprising," or "having" and variations thereof herein is meant to encompass the items listed thereafter and equivalents thereof as well as additional items. Accordingly, the terms "including," "comprising," or "having" and variations thereof are open-ended expressions and can be used interchangeably herein.

The phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other.

Furthermore, identification references (e.g., primary, secondary, first, second, third, fourth, etc.) are not intended to connote importance or priority but are used to distinguish one feature from another. The drawings are for purposes of illustration only and the dimensions, positions, order and relative sizes reflected in the drawings attached hereto may vary.

Furthermore, the terms "substantial" or "substantially," as well as the terms "approximate" or "approximately," can be used interchangeably in some embodiments, and can be described using any relative measures acceptable by one of ordinary skill in the art. For example, these terms can serve as a comparison to a reference parameter, to indicate a deviation capable of providing the intended function. Although non-limiting, the deviation from the reference parameter can be, for example, in an amount of less than 1%, less than 3%, less than 5%, less than 10%, less than 15%, less than 20%, and so on.

Still furthermore, although the various methods disclosed herein are described as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure. Furthermore, the methods may be implemented in association with the formation and/or processing of structures illustrated and described herein as well as in association with other structures not illustrated.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, the present disclosure has been described herein in the context of a particular implementation in a particular environment for a particular purpose. Those of ordinary skill in the art will recognize the usefulness is not limited thereto and the present disclosure may be beneficially implemented in any number of environments for any number of purposes. Thus, the claims set forth below are to be construed in view of the full breadth and spirit of the present disclosure as described herein.

What is claimed is:

1. A pump, comprising:
   a pump chamber operably coupled with a piston;
   a sensor; and
   a piston grip coupled to the piston and comprising a sensor plate having an opening, wherein movement of the piston grip causes the piston to move axially relative to the pump chamber to control receipt and delivery of a liquid drug and wherein the opening is aligned with the sensor during a part of the movement of the piston grip.

2. The pump of claim 1, wherein the sensor plate is provided at a fixed position on the grip body and the opening moves relative to the sensor plate.

3. The pump of claim 1, the piston grip further comprising a solid portion that is aligned with the sensor during a second part of the movement of the piston grip.

4. The pump of claim 1, wherein the sensor plate is provided distal of the piston.

5. The pump of claim 1, wherein the sensor is an optical sensor and the pump further comprises a light source.

6. The pump of claim 5, wherein the optical sensor comprises a photodiode.

7. The pump of claim 1, the piston grip comprising a grip body extending on opposite sides of the piston.

8. The pump of claim 1, further comprising a sensor block configured to position the sensor proximate to the piston grip.

9. The pump of claim 1, further comprising a set of side springs coupled to the piston grip, wherein the set of side springs provide a spring force to bias the piston grip toward the pump chamber.

10. A reciprocating pump, comprising:
    a pump chamber operably coupled with a piston;
    a sensor; and
    a piston grip coupled to the piston and comprising a sensor plate having an opening, wherein movement of the piston grip causes the piston to move axially relative to the pump chamber to control receipt and delivery of a liquid drug.

11. The reciprocating pump of claim 10, wherein the opening is aligned with the sensor during a part of the movement of the piston grip.

12. The reciprocating pump of claim 10, wherein the sensor plate is provided at a fixed position on the grip body and the opening moves relative to the sensor plate.

13. The reciprocating pump of claim 10, the piston grip further comprising a solid portion that is aligned with the sensor during a part of the movement of the piston grip.

14. The reciprocating pump of claim 10, wherein the sensor plate is provided distal of the piston.

15. The reciprocating pump of claim 10, wherein the sensor is an optical sensor and the pump further comprises a light source.

16. The reciprocating pump of claim 15, wherein the optical sensor comprises a photodiode.

17. The reciprocating pump of claim 10, the piston grip comprising a grip body extending on opposite sides of the piston.

18. The reciprocating pump of claim 10, further comprising a sensor block configured to position the sensor proximate to the piston grip.

19. The reciprocating pump of claim 10, further comprising a set of side springs coupled to the piston grip, wherein the set of side springs provide a spring force to bias the piston grip toward the pump chamber.

* * * * *